US006599754B2

(12) United States Patent
Miller et al.

(10) Patent No.: US 6,599,754 B2
(45) Date of Patent: Jul. 29, 2003

(54) BIPHASIC REACTION VESSEL AND METHODS OF USE

(75) Inventors: Benjamin L. Miller, Rochester, NY (US); Bryan Klekota, Del Mar, CA (US)

(73) Assignee: University of Rochester, Rochester, NY (US)

( * ) Notice: Subject to any disclaimer, the term of this patent is extended or adjusted under 35 U.S.C. 154(b) by 77 days.

(21) Appl. No.: 09/838,971

(22) Filed: Apr. 20, 2001

(65) Prior Publication Data

US 2002/0085955 A1 Jul. 4, 2002

Related U.S. Application Data

(60) Provisional application No. 60/198,953, filed on Apr. 21, 2000.

(51) Int. Cl.[7] .................................................. C01N 1/18
(52) U.S. Cl. ...................... 436/178; 436/177; 436/501; 436/514
(58) Field of Search ................................ 436/177, 178, 436/501, 514

(56) References Cited

U.S. PATENT DOCUMENTS

| 4,289,917 A | | 9/1981 | Kane et al. |
| 4,666,672 A | * | 5/1987 | Miller et al. ............. 422/82.07 |
| 5,002,871 A | * | 3/1991 | Iacobucci .................. 435/68.1 |
| 5,219,733 A | | 6/1993 | Myojo et al. |
| 5,478,730 A | | 12/1995 | Alakhov et al. |
| 5,501,841 A | * | 3/1996 | Lee et al. .................... 422/101 |
| 5,525,475 A | * | 6/1996 | Ladouceur .................. 435/7.9 |
| 6,107,055 A | * | 8/2000 | Bauer et al. ............... 435/68.1 |

FOREIGN PATENT DOCUMENTS

EP       1061128 A1    12/2000

OTHER PUBLICATIONS

Nazarpack–Kandlousy et al. "Synthesis and Characterization of a Mixture–Based Library of Oxime Ethers Based on a Common Aromatic Scaffold", J. Comb. Chem., 1999, v. 1, pp. 199–206.*

* cited by examiner

*Primary Examiner*—T. Tung
*Assistant Examiner*—Yelena Gakh
(74) *Attorney, Agent, or Firm*—Nixon Peabody LLP

(57) ABSTRACT

A reaction vessel and method of identifying a ligand having affinity for a target molecule are disclosed. The reaction vessel includes a first member defining a first chamber, the first chamber including an organic solvent and a plurality of reactants which form a combinatorial library of products; a second member defining a second chamber, the second chamber including a target molecule and an aqueous solvent immiscible in the organic solvent; and a semipermeable membrane separating the contents of the first chamber from the contents of the second chamber, wherein said semipermeable membrane is permeable to one or more products of the combinatorial library of products.

5 Claims, 13 Drawing Sheets

FIG. 7A
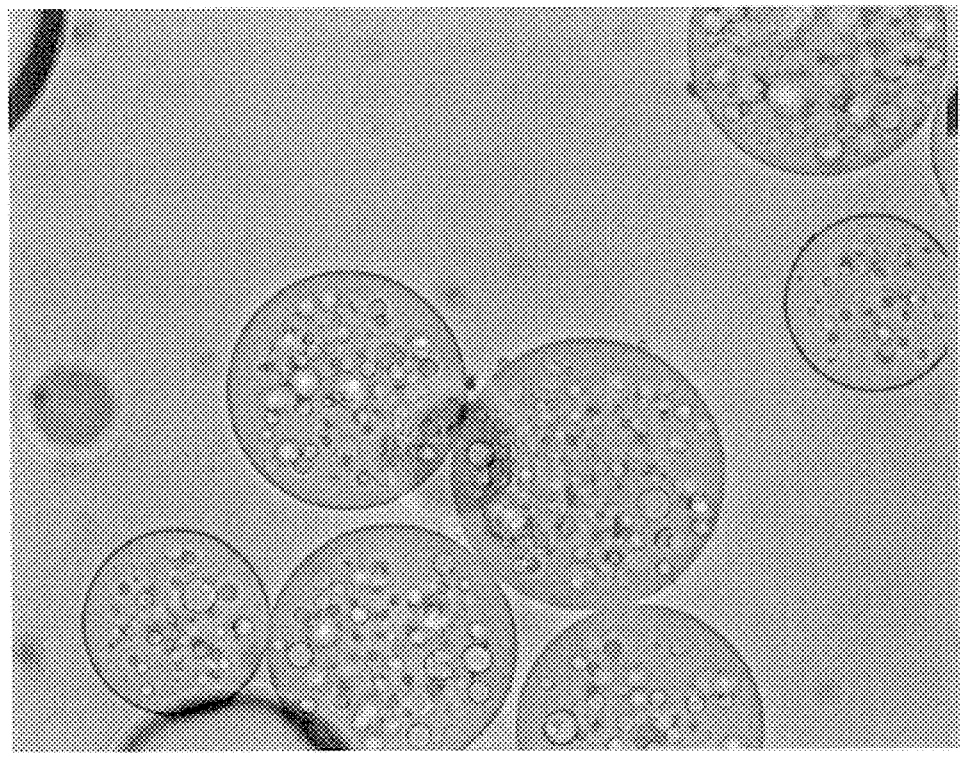
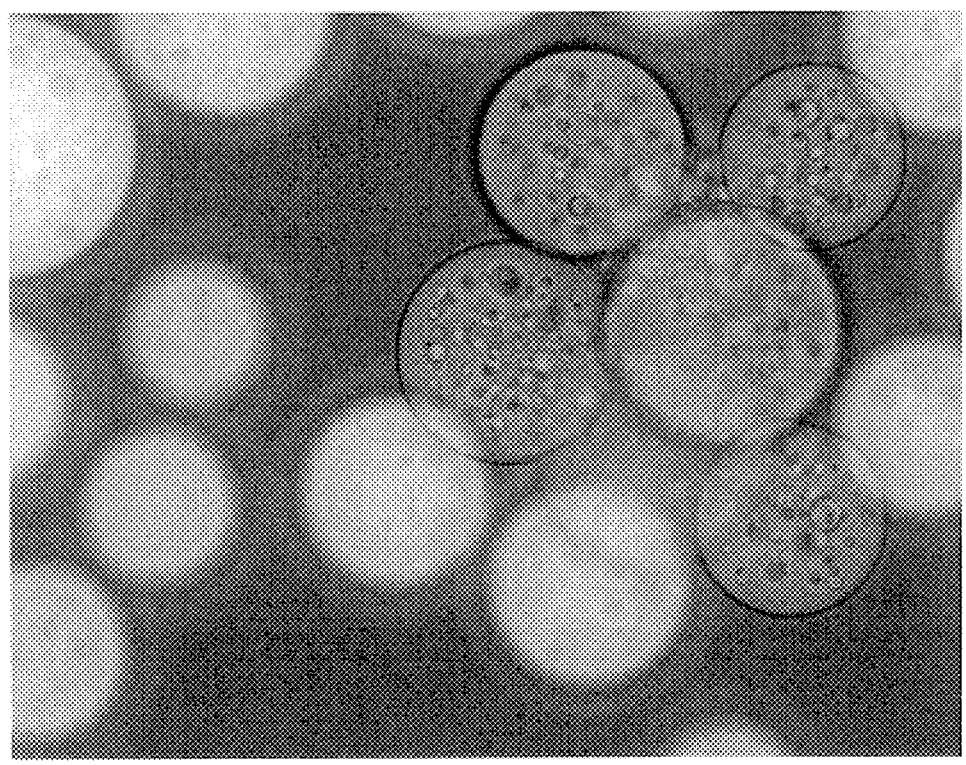
FIG. 7B

FIG. 8A
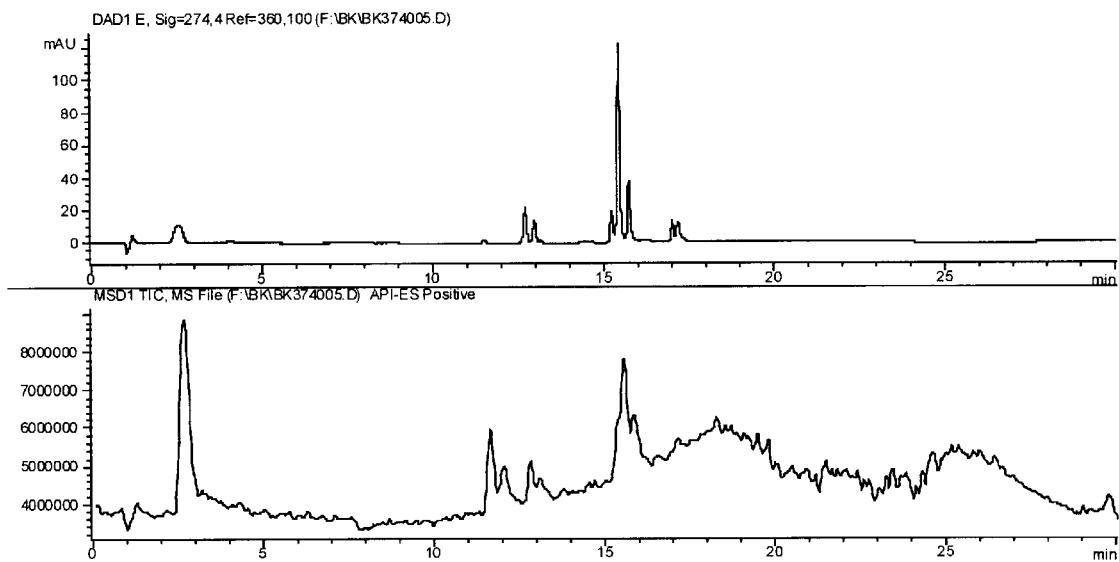
FIG. 8B
FIG. 9A
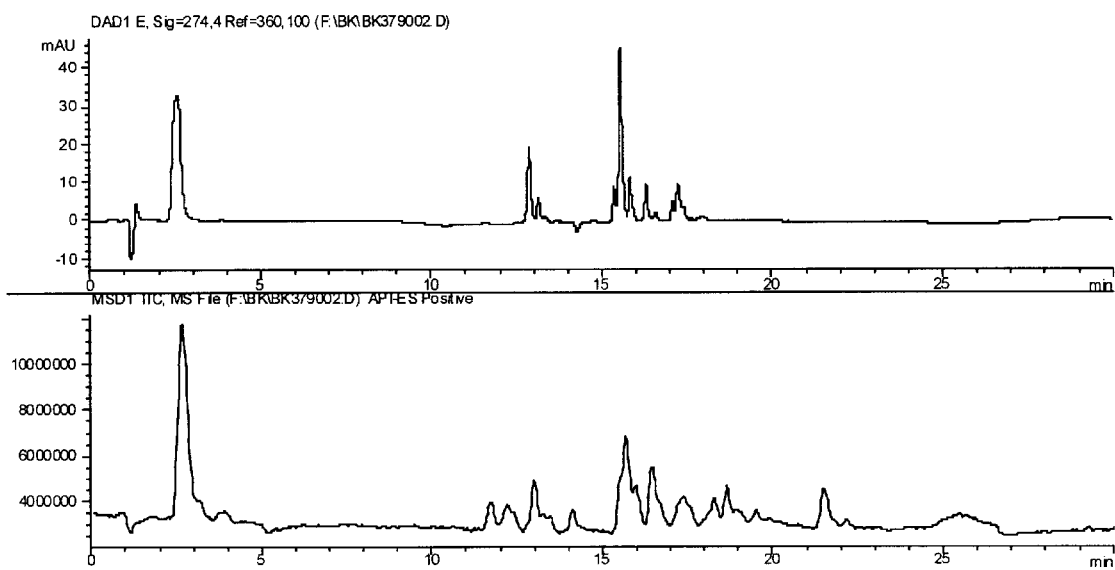
FIG. 9B

FIG. 10A
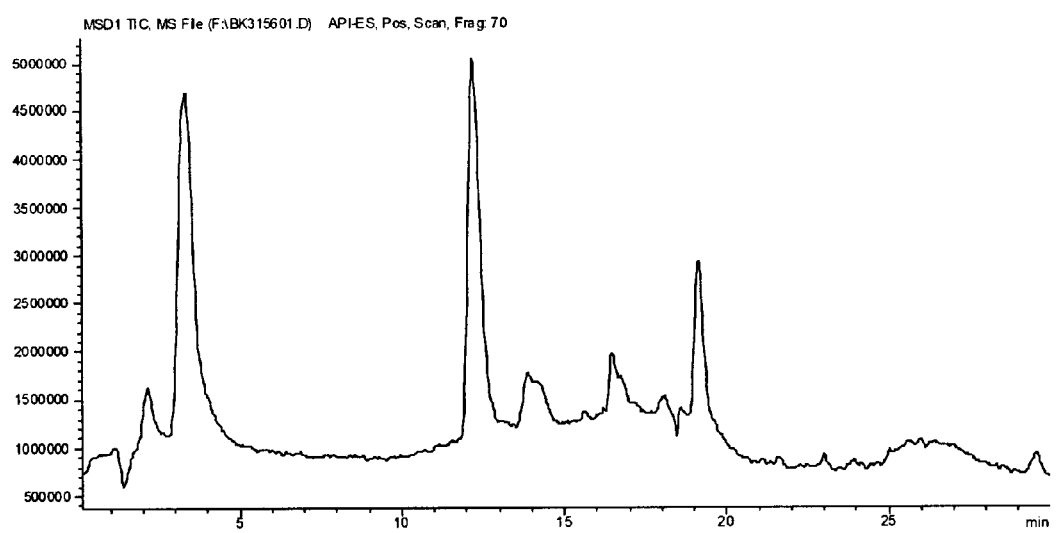
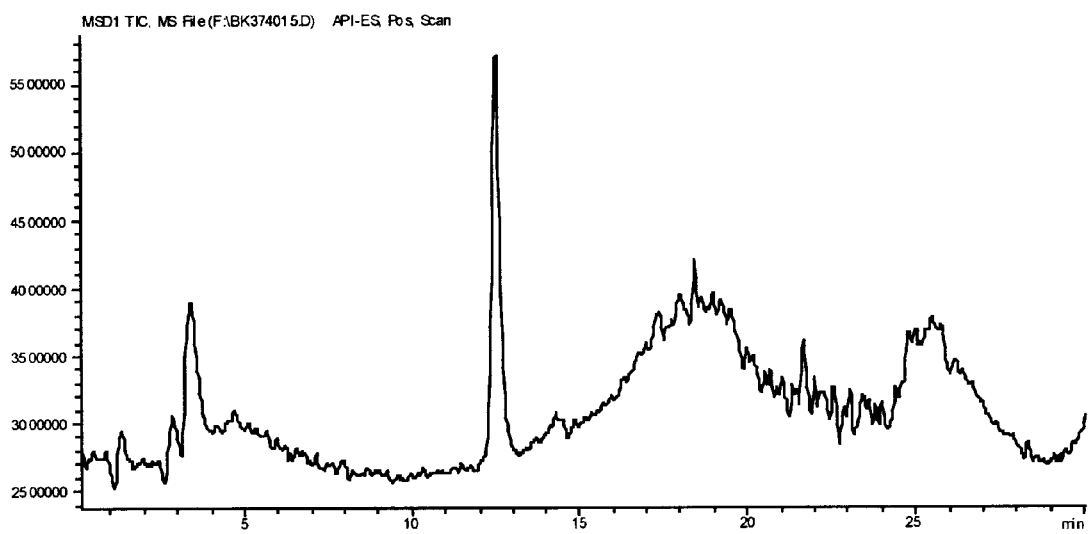
FIG. 10B

FIG. 12A
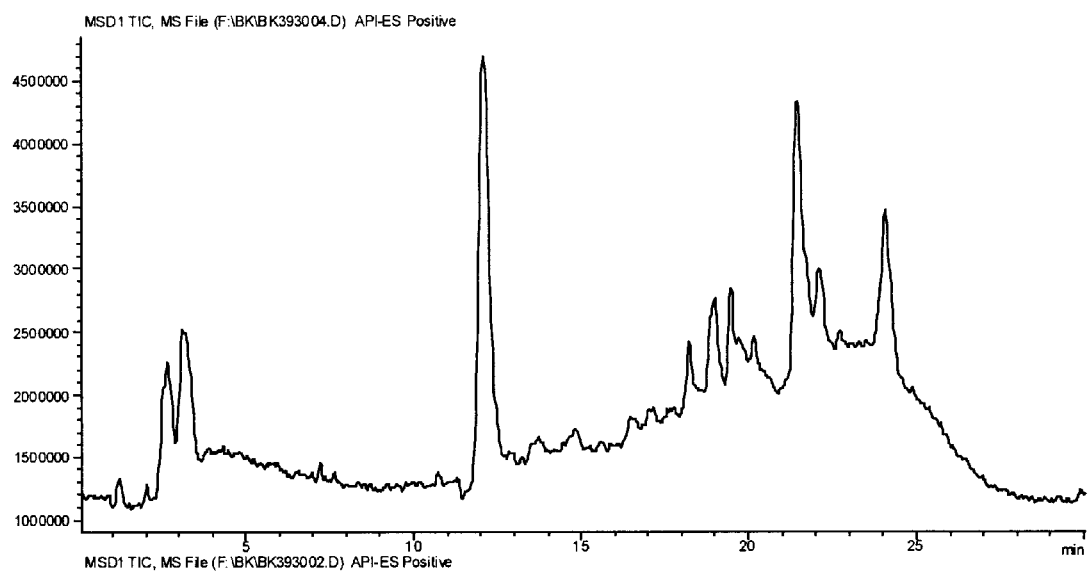
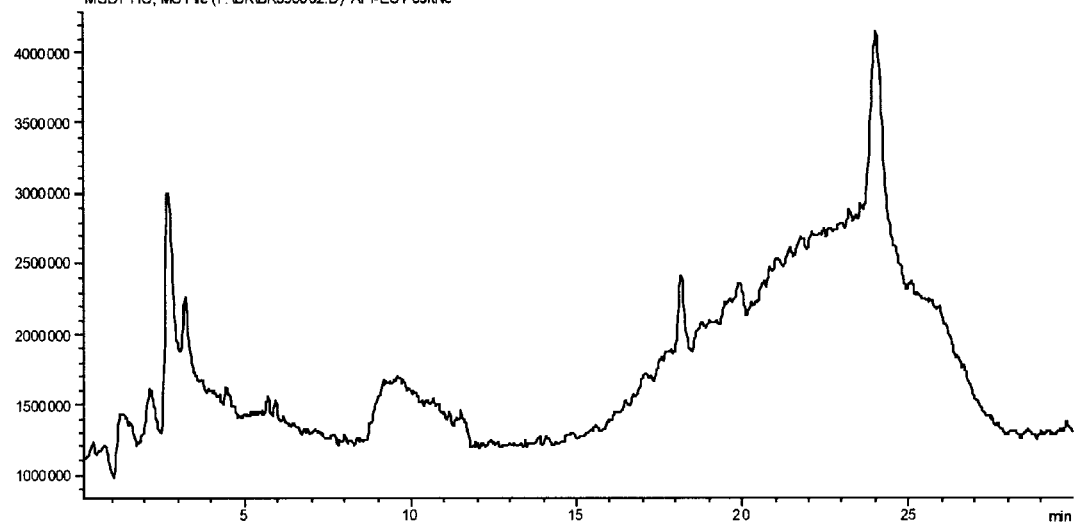
FIG. 12B

FIG. 13A
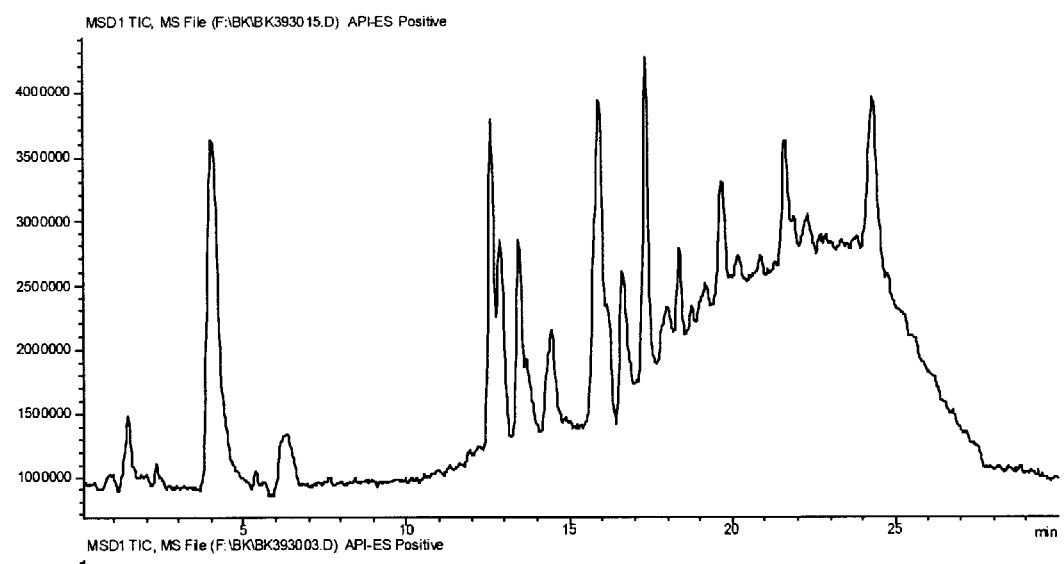
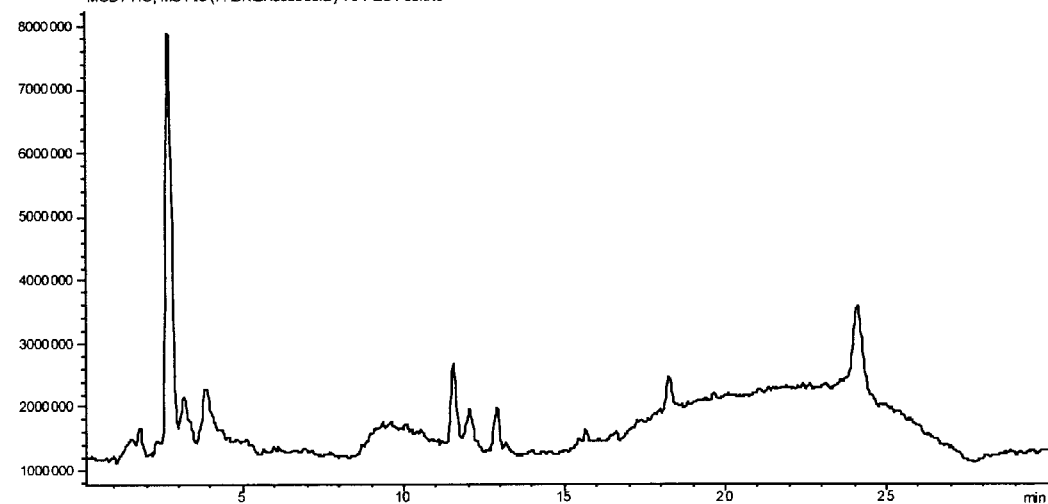
FIG. 13B

BIPHASIC REACTION VESSEL AND METHODS OF USE

This invention claims benefit of U.S. Provisional Patent Application Ser. No. 60/198,953 filed Apr. 21, 2000, which is hereby incorporated by reference in its entirety.

BACKGROUND OF THE INVENTION

In 1999, the synthesis, extraction, and biological screening of organic compounds was estimated to account for over one-quarter of the 24 billion dollars spent on pharmaceutical research and development. Undoubtedly, much of this expense results from inefficiencies in the laboratory and from failed compounds. Contributions that help reduce the cost of lead compound identification, with respect to both financial and time savings, are desirable.

Dynamic combinatorial chemistry offers the advantage of synthesizing a multitude of compounds under equilibrating conditions with simultaneous receptor binding directing the dynamic equilibrium. In practice, the process has several limitations. First, the chemistry which may be employed as a scrambling mechanism (e.g., during self-assembly or otherwise) is limited by target molecule compatibility. Any type of chemistry that can modify the target may lead to a false hit, and render any ligand identified by the assay suspect. In nucleic acid directed libraries, for example, free radical generating and methylating reagents must not be employed. Reactions catalyzed by extremes of pH are also undesirable. Obviously, any limitations on the chemistry involved in this approach detracts from its utility, so it is advantageous to develop a means that enables the use of the maximum number of scrambling reactions. Second, binding assays are typically done in aqueous solution. However, many organic transformations are incompatible with water. More importantly, many organic transformations are reversible and could be used to generate dynamic diversity. Unfortunately, they would not be useful if they could not be performed in aqueous solvent. These two drawbacks present significant limitations to the overall power of dynamic combinatorial chemistry.

The present invention is directed to overcoming the above-identified deficiencies in dynamic combinatorial chemistry and rendering the process of lead compound identification much more efficient.

SUMMARY OF THE INVENTION

One aspect of the present invention relates to a reaction vessel which can be used to identify ligands, which are reaction products of a combinatorial library, that bind to a particular target molecule. The reaction vessel includes a first member defining a first chamber, the first chamber including an organic solvent and a plurality of reactants which form a combinatorial library of products; a second member defining a second chamber, the second chamber including a target molecule and an aqueous solvent immiscible in the organic solvent; and a semipermeable membrane separating the contents of the first chamber from the contents of the second chamber, wherein said semipermeable membrane is permeable to one or more products of the combinatorial library of products.

According to one embodiment, the reaction vessel, absent any reactants, includes: a first reaction container including (i) a body having an open end and (ii) a cap secured about the open end to define a first reaction chamber; and a second reaction container which is sized and configured for placement within the first reaction chamber, the second reaction container including (i) a body having an open end, (ii) a semipermeable membrane positioned over at least a portion of the open end, and (iii) a cap having an aperture therethrough, which cap is secured about the open end with the semipermeable membrane covering the aperture to define a second reaction chamber.

According to a second embodiment, the reaction vessel, absent any reactants, includes: a first reaction container including a body having an open end and defining a first reaction chamber; a second reaction container including a body having an open end and defining a second reaction chamber; and a cap element including (i) a first portion secured about the open end of the first reaction container and having an aperture therethrough, (ii) a second portion secured about the open end of the second reaction container and having an aperture therethrough, and (iii) a semipermeable membrane positioned between the first and second portions and obstructing communication between the apertures thereof.

A further aspect of the present invention relates to a method of identifying a ligand having affinity for a target molecule. This method includes the steps of providing a dual-chambered reaction vessel including first and second containers defining first and second chambers, respectively, which are separated by a semipermeable membrane, with the first chamber including an organic solvent and a plurality of reactants which form a combinatorial library of products, the second chamber including an aqueous solvent immiscible in the organic solvent and, optionally, a target molecule, and the semipermeable membrane being permeable to one or more products of the combinatorial library of products; and identifying any products present in the second chamber at higher concentration while the target molecule is present than without.

The present invention avoids many problems inherent in dynamic combinatorial chemistry. Library generation is performed in an organic medium that is immiscible with water and separated from the target molecule by a semipermeable membrane. The membrane isolates the target molecule within an aqueous phase by its size, yet allows small molecule ligand transport and diffusion. This approach affords several advantage. First, ligands are assembled in an organic phase, which provides a wide range of organic reactions and catalysts that are unsuccessful in water. Thus, chemical reactions which mutate the library are carried out in an environment which is isolated from the target molecule, thereby ensuring that the target molecule is not somehow chemically modified and bolstering confidence in the accuracy of binding assays. Second, in theory any reversible reaction can be employed. This allows for use of catalyzed forward and reverse reactions during assembly and disassembly of combinatorial products, as well as coordination chemistry of the type disclosed, for example, in U.S. patent application Ser. No. 09/181,108 to Miller et al., filed Oct. 28, 1998, which is hereby incorporated by reference in its entirety. Third, bimolecular reactions can be concentrated, guaranteeing a reaction rate that is faster than ligand-target molecule dissociation rate. This provides for affinity-based enrichment of the library products present in the aqueous phase.

BRIEF DESCRIPTION OF THE DRAWINGS

FIG. 3A is an exploded view of the reaction vessel. FIG. 3B shows an assembled small reaction container, a liquid chromatography-mass spectrometry (LC-MS) vial, with a semipermeable membrane placed over the opening to the vial and a cap crimped over the end with the vial opening.

FIGS. 7A–B illustrate the reversibility of the Pd (0) catalyzed reaction. In FIG. 7A, acetoxycyclopent-2-ene derivatized Wang resin beads are shown. In FIG. 7B, derivatived beads are shown after 24 hours under palladium chemistry conditions (dark beads are un-derivatized Wang resin added after reaction for 24 hours).

FIGS. 8A–B are chromatographs comparing UV and LC-MS detection. FIG. 8A illustrates UV absorbance at 274 nm, whereas FIG. 8B illustrates total ion chromatogram (electrospray positive ionization).

FIGS. 9A–B illustrate, respectively, the UV and LC-MS analysis of reaction products while measuring activity of the Pd(0) catalyst.

FIGS. 10A–B illustrate the palladium catalyst lifetime, comparing test conditions in the presence of palladium catalyst (10A) and in the absence of palladium catalyst (10B).

FIGS. 12A–B are LC-MS chromatographs which demonstrate membrane permeability for 1,4-diacetoxy cyclopent-2-ene and methoxyphenylacetic acid. FIG. 12A is a total ion chromatogram (ES+) from methylene chloride. FIG. 12B is a total ion chromatogram from water.

FIGS. 13A–B are chromatographs illustrating successful palladium reaction in the presence of water. FIG. 13A illustrates a sample from the organic compartment and FIG. 13B illustrates a sample from the aqueous compartment.

DETAILED DESCRIPTION OF THE INVENTION

Figure 1:
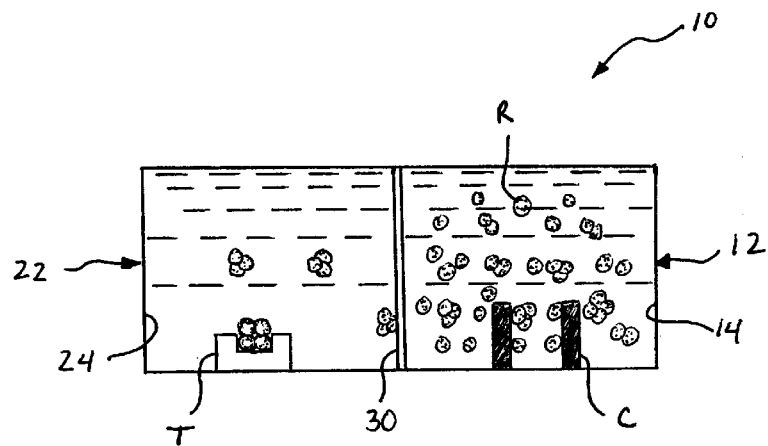
FIG. 1 is a schematic representation of a reaction vessel of the present invention which includes a reaction or scrambling chamber in which dynamic combinatorial reactions take place to form reaction products of a combinatorial library and a binding chamber in which a target molecule resides, shifting the equilibrium of the dynamic combinatorial reactions toward the production of reaction products having an affinity for the target molecule. The two chambers are separated by a semipermeable membrane, which allows separation of the organic phase (in which the dynamic combinatorial reactions take place) from the aqueous phase (in which binding of reaction products to the target molecule can occur).

Referring to FIG. 1, a reaction vessel 10 of the present invention includes a first member 12 defining a first chamber 14, a second member 22 defining a second chamber 24, and a semipermeable membrane 30 separating the contents of the first chamber from the contents of the second chamber.

In use, the first chamber will include an organic solvent and a plurality of reactants R which form a combinatorial library of products. The first chamber may also include a solid-phase or solubilized catalyst C to allow self-assembly and/or disassembly of the combinatorial library of products. The second chamber will include a target molecule T present in an aqueous solvent which is immiscible in the organic solvent. The semipermeable membrane 30 is permeable to one or more products of the combinatorial library of products, allowing separate equilibria to develop in the aqueous phase and the organic phase. The presence of the target molecule T in the aqueous phase will affect the dynamic equilibrium of the combinatorial reaction occurring in the organic phase. (However, in a control reaction vessel, no target molecule will be present to affect the dynamic equilibrium of the combinatorial library.)

Generally, the first and second members 12 and 22, respectively, are formed of inert materials which will not interfere with the chemistry occurring in the respective chambers thereof. Thus, the inert material should resist degradation by a selected solvent. Possible degradation of the material used to form the first and second members 12 and 22 is typically only an issue for selected organic solvents. Suitable inert materials for both the first and second members 12 and 22 include glass, pyrex, and thermoplastic materials such as polyethylene.

As noted above, the semipermeable membrane 30 is permeable to one or more products of the combinatorial library of products. Suitable semipermeable membranes can be selected based not only on their permeability, but also based on their durability with respect to one or more organic solutions (i.e., used in the organic phase). The appropriateness of various membrane substrates with selected organic solvents or reagents is well known and such information can be accessed from commercial membrane distributors, such as Spectrum Laboratories, Inc. (Rancho Dominquez, Calif.) and Whatman, Inc. (Clifton, N.J.).

Typically, the semipermeable membrane is characterized by permeability to products of the combinatorial library having a molecular weight of less than about 10,000 daltons, preferably less than about 5,000 daltons, and more preferably less than about 1,000 daltons. The specific permeability requirements of the membrane will depend, at least in part, on the size of the target molecule. The semipermeable membrane should be selected so that the target molecule is retained in the aqueous phase.

Any membrane which satisfies both the permeability and durability criteria can be utilized in the reaction vessel of the present invention. Suitable semipermeable membrane materials include, without limitation, cellulose and nylon. Various cellulose membranes having both the desired permeability and durability are commercially available from Spectrum Laboratories, Inc. Exemplary cellulose membranes include Spectra/Por 3 (Spectrum Laboratories Cat. No. 132724; MWCO of about 3.5 kDa) and Spectra/Por 6 (Spectrum Laboratories Cat. No. 132638; MWCO of about 1.0 kDa). Nylon membranes having both the desired permeability and durability are commercially available from Whatman, Inc.

Figure 2:
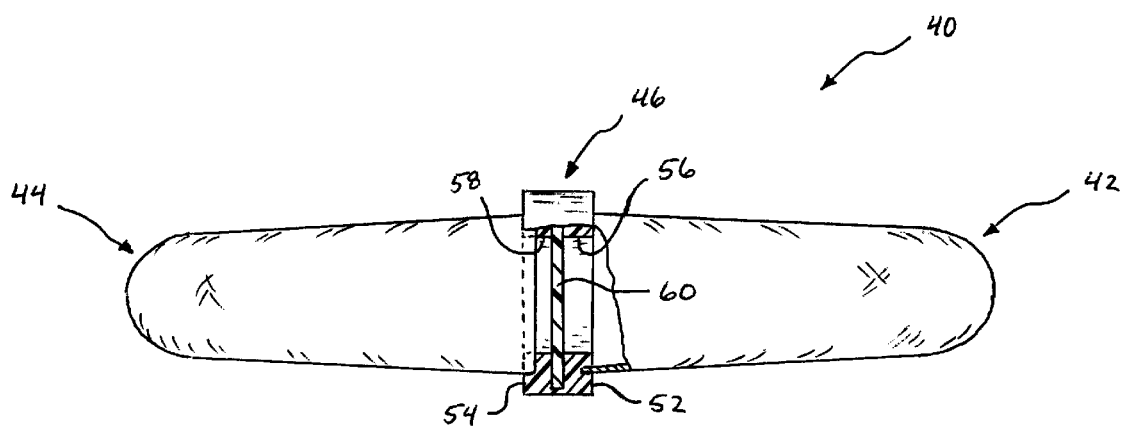
FIG. 2 is a side elevational view of a reaction vessel according to one embodiment of the present invention, including two reaction containers and a single cap element which can be placed onto their respective open ends. Part of the cap element is broken away to expose the semipermeable membrane captured between first and second portions of the cap element. In use, the semipermeable membrane separates the contents of the two reaction containers.

One embodiment of the reaction vessel (excluding the organic phase, reactants R, aqueous phase, and target molecule T) is shown in FIG. 2. The reaction vessel 40 includes a first reaction container 42, a second reaction container 44, and a cap element 46.

The first reaction container 42 has a body with an open end and defines a first reaction chamber. Likewise, the second reaction container 44 has a body with an open end and defines a second reaction chamber. Suitable first and second reactions containers can be Eppendorf tubes or other similar containers.

The cap element 46 includes a first portion 52 and a second portion 54, with a semipermeable membrane 60 captured between the first and second portions. The first and second portions 52 and 54 each include an aperture 56 and 58, respectively, extending axially therethrough with the semipermeable membrane obstructing communication between their respective apertures. The cap element 46 can be fabricated by securing together the first and second portions 52 and 54 such that they form a single, unitary structure. The first and second portions 52 and 54 can be secured together using, for example, suitable adhesives, soldering, sonic welding, etc.

The particular design or construction of the first and second portions 52 and 54 will depend on the type of reaction containers employed in the construction of the reaction vessel 40. When Eppendorf tubes are utilized, matching Eppendorf caps should be utilized for preparing the first and second portions of the cap element 46. The aperture of each cap portion can be prepared by drilling the aperture through the Eppendorf caps, followed by securing two such modified Eppendorf caps together as described above, capturing the semipermeable membrane between the first and second portions 52 and 54. Alternatively, Eppendorf caps can be manufactured to include an aperture, in which case the first and second portions of the cap element 46 can simply be secured together, as described above, with the membrane 60 captured between them.

In use, the cap element 46 is installed (i.e., by snap fit) onto the open ends of the first and second reaction containers 42 and 44, thereby placing the semipermeable membrane between the contents of the first and second reaction containers. The cap element 46 has a sufficiently tight fit such that the contents do not leak from the reaction containers 42 and 44. Because the first and second reactions containers are substantially the same, either the organic phase or the aqueous phase can be present in the first reaction container with the other phase being in the second reaction container.

Figure 3A:
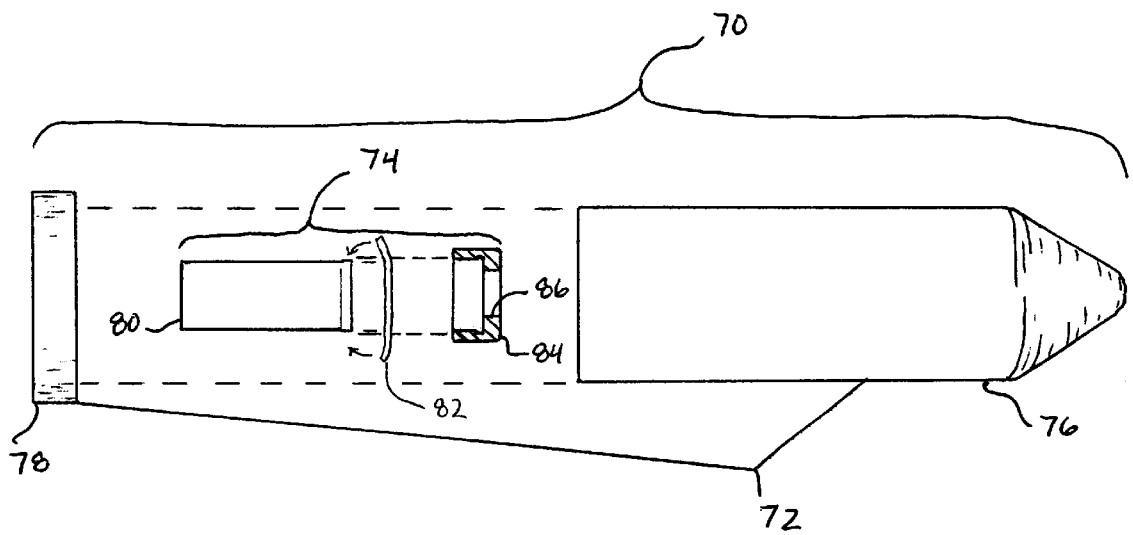
FIGS. 3A–B illustrate a reaction vessel according to another embodiment of the present invention, including a large reaction container and a small reaction container. Each reaction container has its own cap, although the small reaction container is intended to be placed into the reaction chamber of the large container. The cap for the small reaction container contains an aperture and a semipermeable membrane positioned inside the cap (i.e., over the mouth of the small container) separates the contents of the small container from the contents of the large container.
Figure 3B:
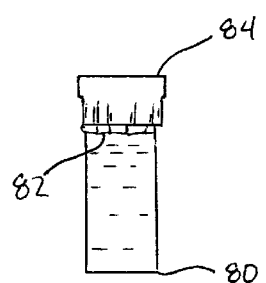

Another embodiment of the reaction vessel (excluding the organic phase, reactants R, aqueous phase, and target molecule T) is shown in FIGS. 3A–B. The reaction vessel 70 includes a first reaction container 72 and a second reaction container 74.

The first reaction container 72 has a body 76 with an open end and a cap 78 secured about the open end to define a first reaction chamber. One type of suitable first reaction container is a centrifuge tube, typically formed of polyethylene.

The second reaction container 74 has a body 80 with an open end, a semipermeable membrane 82 positioned over at least a portion of the open end, and a cap 84 having an aperture 86 therethrough, which cap is intended to be secured about the open end with the semipermeable membrane covering the aperture to define a second reaction chamber. Preferably, the semipermeable membrane covers the entire open end (and has excess membrane extending partially below the open end, see FIG. 3B). The cap 84 can be secured either by snap fit or by crimping the cap to form a tight seal. The second reaction container 74 is sized and configured for placement within the first reaction chamber. One type of suitable second reaction container is an LC-MS vial, typically formed of glass. When and LC-MS vial is utilized, the cap 84 is typically secured by crimping (see FIG. 3B).

In use, the second reaction container 74 is assembled and then placed into the reaction chamber of the first reaction container 72. The semipermeable membrane of the assembled second reaction container separates the contents of the first and second reaction containers. The cap 78 is then placed onto the open end of the first reaction container 72 to seal the reaction chamber closed.

According to one approach, the organic phase is introduced into the second reaction container 74 and the aqueous phase is introduced into the first reaction container 72. Thus, aqueous phase is present in a substantially greater volume than the organic phase. Excess aqueous phase allows more of the reaction products of the combinatorial library to diffuse across the semipermeable membrane before solvent saturation in the aqueous phase is reached. Therefore, this approach is preferred.

According to another approach, the aqueous phase is introduced into the second reaction container 74 and the organic phase is introduced into the first reaction container 72. In this situation, the organic phase is present in a substantially greater volume than the aqueous phase. This arrangement may be desirable when solubility of the reactants or combinatorial library is low in the organic phase relative to their solubility in the aqueous phase.

Regardless of the location of the aqueous phase (i.e., in the first or second reaction containers), the target molecule can, in certain circumstances, be bound to an inert substrate such as glass beads or the like.

A further aspect of the present invention relates to a method of identifying a ligand having affinity for a target molecule. This method is carried out by providing a dual-chambered reaction vessel of the present invention, with the first chamber including an organic solvent and a plurality of reactants which form a combinatorial library of products, the second chamber including an aqueous solvent immiscible in the organic solvent and, optionally, a target molecule, and the semipermeable membrane being permeable to one or more products of the combinatorial library of products; and then identifying any products present in the second chamber at higher concentration while the target molecule is present than without.

Basically, this method is carried out as two separate trials, a first trial where the target molecule is present and a second trial (control) where the target molecule is absent. Any identified products which are present at higher concentration in the first trial as compared to the second trial are ligands of the test molecule. Preferably, the contents of the first and second reaction chambers are allowed to achieve equilibrium before any identification occurs. Typically, identification will be performed after about 20 minutes to about 24 hours following the start of the dynamic combinatorial reaction. Depending upon the nature of the dynamic combinatorial reaction and the affinity of ligands for target molecules, more or less time may be required for equilibrium to be reached. During the time course of the dynamic equilibrium reaction, mild shaking can be carried out to ensure adequate mixing.

Identification of ligands can be carried out according to a number of known procedures. According to one approach, LC-MS is performed on the aqueous phase (i.e., the contents removed from the second reaction container) in the first and second trials, and then it is determined whether the spectroscopy results differ for the first and second trials.

Differences are detected by defining differential MS peaks. First, mass spectroscopy peaks are assigned to predicted combinatorial library products. Next, the assigned mass spectroscopy peaks are matched to the differential peaks recording when comparing the results of the first and second trials.

Once individual compounds having an affinity for the target molecule are identified, such compounds can then be studied using formal binding studies to determine, e.g., the affinity of the compound for the target molecule using competitive inhibitors, the specificity of the compound for the target molecule, etc.

The reaction vessels and methods of the present invention can be utilized with most any dynamic combinatorial libraries as long as at least some, and preferably substantially all, of the reaction products of the library are capable of diffusing through the semipermeable membrane.

The combinatorial library will include a plurality of reaction products each including one or more functional groups or regions capable of interacting with a target molecule. The target molecule can be a receptor molecule, preferably a biological receptor molecule such as a protein, RNA molecule, or DNA molecule. In practice, the target molecule is one which is associated with a particular disease state and, therefore, is considered an active site for targeted therapeutic applications.

The number of reaction products prepared in the combinatorial library will depend on the number of reactants introduced into the library and the chemistry utilized as a scrambling mechanism for reversible binding of individual reactants to one another.

As demonstrated hereinafter, one approach for the combinatorial library is to utilize a molecular scaffold which includes one or more functional groups, preferably two or more functional groups, capable of reacting with one or more members of a diversity pool which includes a plurality of compounds having one or mote functional groups capable of forming a reversible covalent bond with the one or more functional groups of the molecular scaffold. Depending on the particular functional groups which are employed in the reaction of the molecular scaffold with the one or more members of the diversity pool, a solid-phase or solubilized catalyst can be employed to facilitate the forward and reverse reactions between molecular scaffolds and compounds of the diversity pool.

Suitable scaffolds can be selected based upon the particular target molecule which is to be used for binding study with the combinatorial library in the reaction vessel of the present invention. Functional groups on the scaffolds can include, without limitation, amines, carboxylates, olefins, alcohols, thiols, 1,3-dicarbonyls, aldehydes, and allylic esters. If two or more functional groups are present on the scaffold, the two or more functional groups can be the same or different.

Suitable compounds which can be used in a diversity pool should include the one or more functional groups which can interact with the functional groups of the scaffold. Functional groups on members of the diversity pool can include, without limitation, amines, carboxylates, olefins, alcohols, thiols, 1,3-dicarbonyls, aldehydes, and allylic esters.

Suitable catalysts should be selected in conjunction with the types of functional groups being employed on the scaffold and the members of the diversity pool. Exemplary catalysts include, without limitation, palladium catalysts, olefin metathesis catalysts (i.e., bis(tricyclohexylphosphine) benzylidine ruthenium (IV) dichloride), peptidases, lipases, phosphatases, ion-exchange resins (for example, Amberlite IRA-743, Amberlite IRA-900, Amberlite IRC-50, Amberlite IRP-64, Amberlite IRP-69, or Amberlyst A-21, all products of the Aldrich Chemical Company).

Another approach for the combinatorial library is to utilize a metal atom or metal ion as a complexing agent which is capable of forming a labile coordinate bond with one or more members of a diversity pool. The members of the diversity pool are characterized by one or more functional groups capable interacting with the complexing agent to form the labile coordinate bond and one or more recognition elements which can recognize a target molecule (e.g., biological receptor molecule). Exemplary dynamic combinatorial libraries of this type are described in U.S. patent application Ser. No. 09/181,108 to Miller et al., filed Oct. 28, 1998, which is hereby incorporated by reference in its entirety.

Regardless of the type of combinatorial library utilized in a reaction vessel of the present invention, there are preferably at least four reactants present (e.g., one scaffold or complexing agent and three of more compounds of the diversity pool). Assuming each scaffold or complexing agent can associate with at most two members of the diversity pool, then a minimum of nine possible reaction products, excluding stereoisomers, may be present in the combinatorial library. To afford larger libraries, then larger diversity pools (e.g., at least ten compounds, more preferably at least fifteen compounds) can be selected. In addition, scaffolds with more than two reactive groups can also be used, affording more diverse combinatorial libraries even though the diversity pool of reactants may be the same.

EXAMPLES

The following examples are provided to illustrate an embodiment of the present invention but is by no means intended to limit its scope.

Materials & Methods

Carboxylic acids were purchased from the Aldrich Chemical Co. ("Aldrich") and used without further characterization. Methylene chloride was purchased from Sigma Chemical Co. ("Sigma") and distilled over calcium hydride prior to use. Chelex resin was purchased from J. T. Baker. Phosphate Buffered Saline (PBS) was prepared according to standard protocols from materials purchased from Sigma and sterilized prior to use. Deionized water was subjected to redistillation in an all-glass apparatus prior to use. Trypsin was purchased from Sigma. HPLC grade acetonitrile was purchased from Aldrich.

LC-MS was carried out using a Hewlett-Packard Series 1100 MSD, using electrospray ionization in positive ion mode and a Waters C18 reverse-phase column.

NMR spectra were recorded on a Bruker AMX or Bruker Avance spectrometer operating at 400 MHz.

Control experiments: 1,4-diacetoxycyclopent-2-ene, methoxyphenylacetic acid, hydrocinnamic acid, and triethyl phosphite were weighed in 4 mL vials in the open atmosphere. Palladium tetrakistriphenylphosphine was added to the vial containing triethylphosphite under a nitrogen atmosphere inside a glove box. The reagents were diluted with freshly distilled methylene chloride under the nitrogen atmosphere. Stock solutions of 1,4-diacetoxycyclopent-2-ene (1.2 M), methoxyphenylacetic acid (1.2 M), hydrocinnamic acid (1.2 M), and palladium tetrakistriphenylphosphine (90 mM) with triethyl phosphite (360 mM) were prepared. 1,4-diacetoxycyclopent-2-ene (100 µL), methoxyphenylacetic acid (100 µL), and catalyst (40 µL) were added to an LC-MS vial and sealed with a crimper cap. Hydrocinnamic acid (100 µL) was added after specified time periods.

Selection experiments: 1,4-diacetoxycyclopent-2-ene, methoxyphenylacetic acid, hydrocinnamic acid, isovaleric acid, 4-pentynoic acid, cyclopentane carboxylic acid, cis-pinonic acid, tetrahydro-2-furoic acid, 2 -phenylpropionic acid, 2-cyclopentene-1-acetic acid, (–)-methoxyacetic acid and triethyl phosphite were weighed in 4 mL vials in the open atmosphere. Palladium tetrakistriphenylphosphine was added to the vial containing triethylphosphite under a nitrogen atmosphere inside a glove box. The reagents were diluted with freshly distilled methylene chloride under the nitrogen atmosphere. Stock solutions of 1,4 -diacetoxycyclopent-2-ene (2 M), methoxyphenylacetic acid (1.8 M), hydrocinnamic acid (1.8 M), isovaleric acid (1.8 M), 4-pentynoic acid (1.8 M), cyclopentane carboxylic acid (1.8 M), cis-pinonic acid (1.8 M), tetrahydro-2-furoic acid (1.8 M), 2-phenylpropionic acid (1.8 M), 2-cyclopentene-1-acetic acid (1.8 M), (–)-methoxyacetic acid (1.8 M) and palladium tetrakistriphenylphosphine (90 mM) with triethyl phosphite (360 mM) were prepared. An aliquot (611 µL) was removed from each of the ten acid stock solutions, added to a pear shaped flask, and evaporated to dryness. This material was diluted with freshly distilled methylene chloride (4.5 mL) under a nitrogen atmosphere. 1,4-diacetoxycyclopent-2-ene (150 µL), acid stock (750 µL), and catalyst (100 µL) were added to an LC-MS vial, covered with a cellulose membrane and sealed with a crimper cap. The solutions were stirred on a rotary shaker for one hour. The vial was immersed in a centrifuge tube (15 mL) containing 5 mL of PBS buffer pH 7.3. Incubation lasted eighteen hours. The vial was removed from the centrifuge tube. Aqueous solution was frozen to –80° C. and solvent removed in vacuo. Salts remaining after evaporation were washed with acetonitrile (2 mL) and DMSO (100 µL) and filtered through a kimwipe. The organic solvent was evaporated, and the residue diluted with acetonitrile (500 µL). From the methylene chloride solution was removed an aliquot (5 µL) which was filtered through a chelex plug and rinsed with methylene chloride (2 mL). Solvent was removed in vacuo. The residue was diluted with acetonitrile (500 µL).

Organic and aqueous samples were analyzed by electrospray LC-MS in positive ionization mode using an acetonitrile: water 1% trifluoroacetic acid gradient elution (30% CH₃CN—90%).

Example 1
Library Design & Target Selection

Palladium π-allyl substitution reactions were initially selected, because Pd (0) catalysts are known to be air sensitive and this was believed to be a good test of the isolation concept (Wang and Augustine, "A New Type of Heterogeneous Catalyst for Allylic Alkylation Reactions," Chem. Ind. 68:429–433 (1996), which is hereby incorporated by reference in its entirety). It is known that contacting an olefin with a leaving group at the allylic position with a Pd (0) source will generate an electrophilic π-allyl complex (Scheme 1, top). Addition of a nucleophile then will allow for substitution at the allylic position. Furthermore, the reaction can be performed regio- and stereoselectively by using the right choice of chiral ligands (VanVranken and Trost, "Asymmetric Transition Metal-Catalyzed Allylic Alkylations," Chem. Rev. 96:395–422 (1996); Hayashi et al., "Retention of Regiochemistry of Allylic Esters in Palladium-Catalyzed Allylic Alkylation in the Presence of a MOP Ligand," J. Am. Chem. Soc. 120:1681–1687 (1998); Giambastiani and Giovanni, "Palladium Catalyzed Alkylation with Allylic Acetates under Neutral Conditions," J. Org. Chem. 63:9608–9609 (1998), which are hereby incorporated by reference in their entirety). Thus, it was hypothesized that by using nucleophiles with similar reactivity (X, X'), in terms of nucleophilicity and leaving group ability, this reaction could be made to be a reversible, nonselective process as required to generate diversity in a dynamic sense.

Scheme1: Reversible palladium chemistry

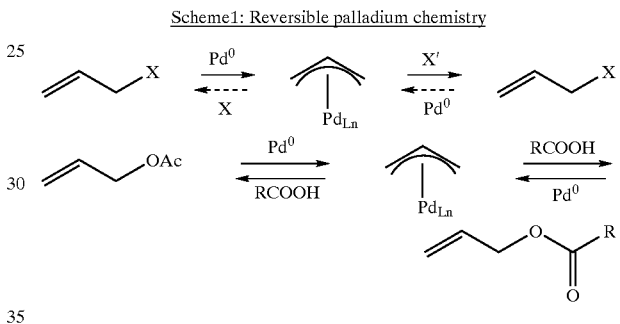

To test this hypothesis, allylic acetates were used as starting materials and carboxylic acids were used as diversity generating nucleophiles as shown in Scheme 1. The rationale for this was as follows: first, acetate is a commonly employed, readily ionizable group in palladium π-allyl chemistry. Second, there are plenty of commercially available carboxylic acids, so obtaining diversity elements for such a system would be trivial. Third, allylic acetates are a general class of compounds that are readily accessible.

Simple allyl substituted carboxylates are not interesting structurally, and did not appear to be promising ligands for either protein or nucleic acid targets. 1,4-diacetocyclopent-2-ene offered some key advantages, which led to its selection as a scaffold (Scheme 2 below). First, it is functionalized at both allylic positions, a structural feature employed by Trost in the synthesis of carbanucleosides (Madsen et al., "Palladium-Catalyzed Enantioselective Synthesis of Carbanucleosides," J. Am. Chem. Soc. 122:5947–5956 (2000), which is hereby incorporated by reference in its entirety). This ability to be functionalized at two positions, as well as potentially forming cis/trans stereoisomers, created the possibility of generating a lot of diversity from a limited number of starting materials. Furthermore, using a large number of carboxylic acids would provide sufficient structural variation for a dynamic diversity experiment. Low affinity compounds, like the starting diacetate, carboxylic acids, and some of the esters would be expected to have weak interactions with the receptor and be quickly released. Other esters would have stronger interactions and remain bound for a period of time. Equilibrium would then shift to favor the synthesis of the high affinity esters.

Scheme 2

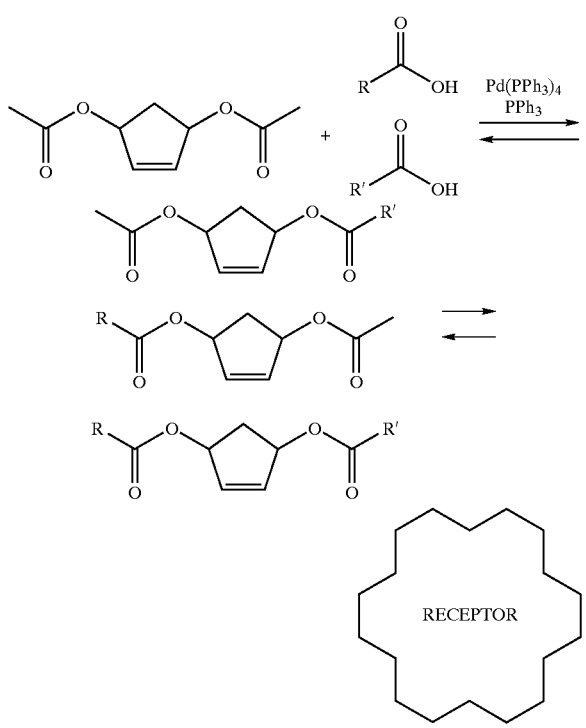

With an interesting scaffold and scrambling mechanism, a target needed to be identified against which these cyclopentene based compounds could be applied. A variety of serine protease inhibitors based on proline derivatives were identified in the literature (Lewis et. al., "Characterization of the Two-Step Pathway for Inhibition of Thrombin by α-Ketoamide Transition State Analogs" *J. Bio. Chem.* 273:4843–4854 (1998), which is hereby incorporated by reference in its entirety). Although these compounds are 1,2 substituted, it was believed that 1,3 substituted compounds might also be useful. The serine proteases constitute a large class of proteins implicated in wide range of disease states (Stroud, "A Family of Protein-Cutting Proteins," *Sci. Am.* 231:74–88 (1974), which is hereby incorporated by reference in its entirety). As such, they have been targeted extensively by the pharmaceutical industry (Babine and Bender, "Molecular Recognition of Protein-Ligand Complexes: Applications to Drug Discovery," *Chem. Rev.* 97:1359–1472 (1997), which is hereby incorporated by reference in its entirety), and a significant amount of structural information is available (Obst et al., "Molecular Recognition at the Thrombin Active Site: Structure-Based Design and Synthesis of Potent and Selective Thrombin Inhibitors and the X-ray Crystal Structures of Two Thrombin-Inhibitor Complexes," *Chemistry & Biology,* 4:287–295 (1997), which is hereby incorporated by reference in its entirety). Ligands in this family encompass a diverse array of molecular structure (Shuman et. al., "Highly Selective Tripeptide Thrombin Inhibitors," *J. Med. Chem.* 36:314–319 (1993); St. Charles et al., "Bound Structures of Novel P3-P1' β-Strand Mimetic Inhibitors of Thrombin," *J. Med. Chem.* 42:1376–1383 (1999); Adang et. al., "Solution-Phase and Solid-Phase Synthesis of Novel Transition State Inhibitors of Coagulation Enzymes Incorporating a Piperidinyl Moiety," *Bioorg. Med. Chem. Lett.* 9:1227–1232 (1999); Ambler et. al., "Optimisation of the P2 Pharmacophore in a Series of Thrombin Inhibitors: Ion-Dipole Interactions with Lysine 60G," *Bioorg. Med. Chem. Lett.* 9:1317–1322 (1999), which are hereby incorporated by reference in their entirety). In that regard, changing the substitution pattern by one position seemed like a relatively small change. Also, trypsin was used rather than thrombin, hoping that these active sites may differ enough so that the slight variation would be better tolerated.

Example 2
Analysis of Combinatorial Library

After designing a suitable dynamic diversity scheme, combinatorial libraries were prepared. A simple library containing 1,4-diacetoxycyclopent-2-ene, seven commercially available carboxylic acids, and the in situ formed acetate, was generated in an organic-aqueous system using the Eppendorf apparatus (FIG. 2) where the solvents were separated by a semi-permeable membrane.

1,4-diacetoxycyclopent-2-ene is a known compound prepared by slightly modified version of literature preparation, by bromination of cyclopentadiene (Young et al., "1,2- and 1,4-Dibromides from Cyclopentadiene," *J. Am. Chem. Soc.* 78:4338–4344 (1956), which is hereby incorporated by reference in its entirety) and conversion to diacetate (Toru et. al., "A New Synthesis of cis-3,5-Diacetoxycyclopentene" *Synthesis* 867–868 (1974), which is hereby incorporated by reference in its entirety).

Figure 4:
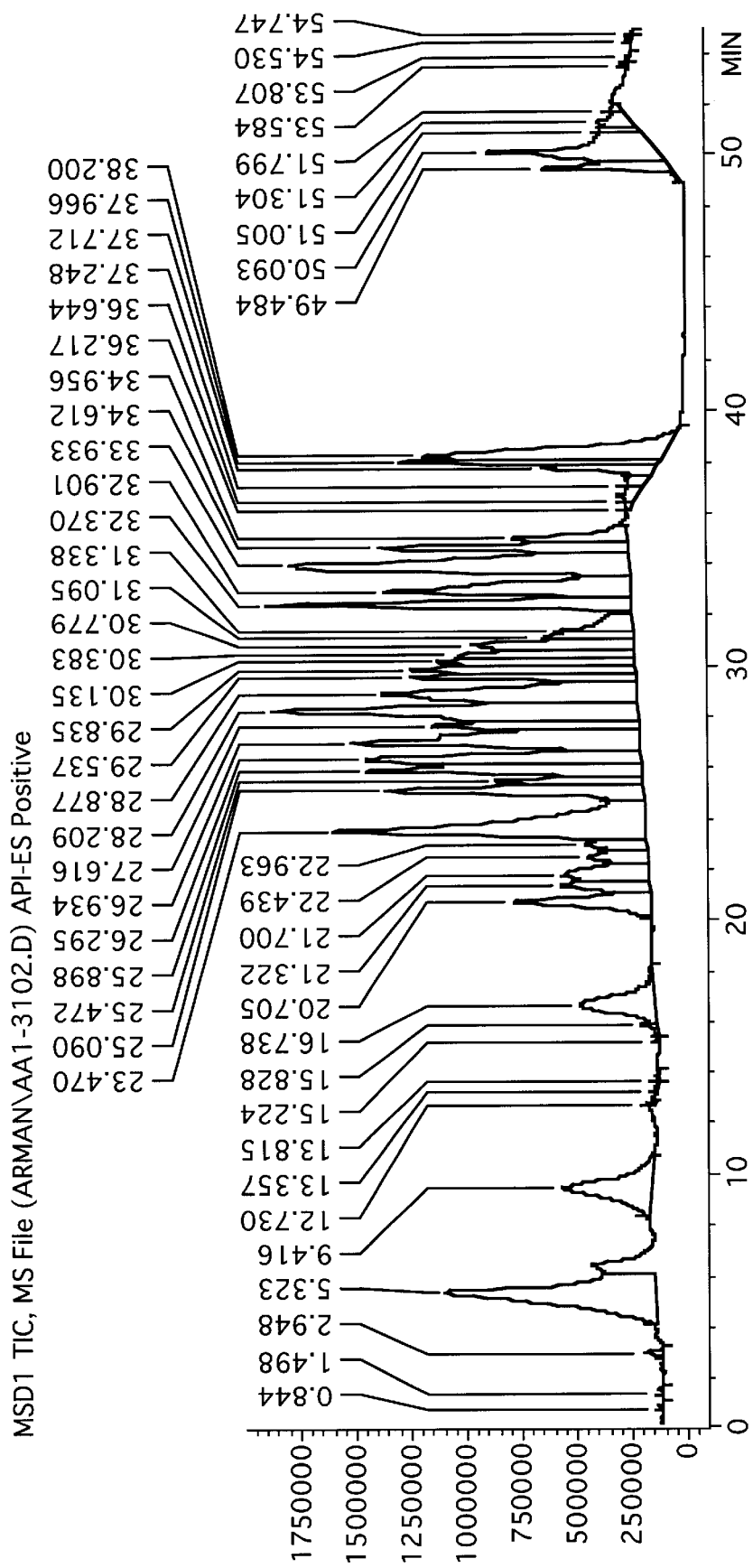
FIG. 4 is an LC-MS chromatograph showing the analysis of a 64 compound library.

An HPLC-MS trace of the organic side is shown in FIG. 4. A library of this size could potentially generate sixty-four cyclopentene based di-esters, ignoring stereoisomers. The large number of peaks in the trace in FIG. 4 suggested that a significant proportion of the possible compounds were formed, based on expected molecular weights (MS peaks) for the library members.

Figure 5:
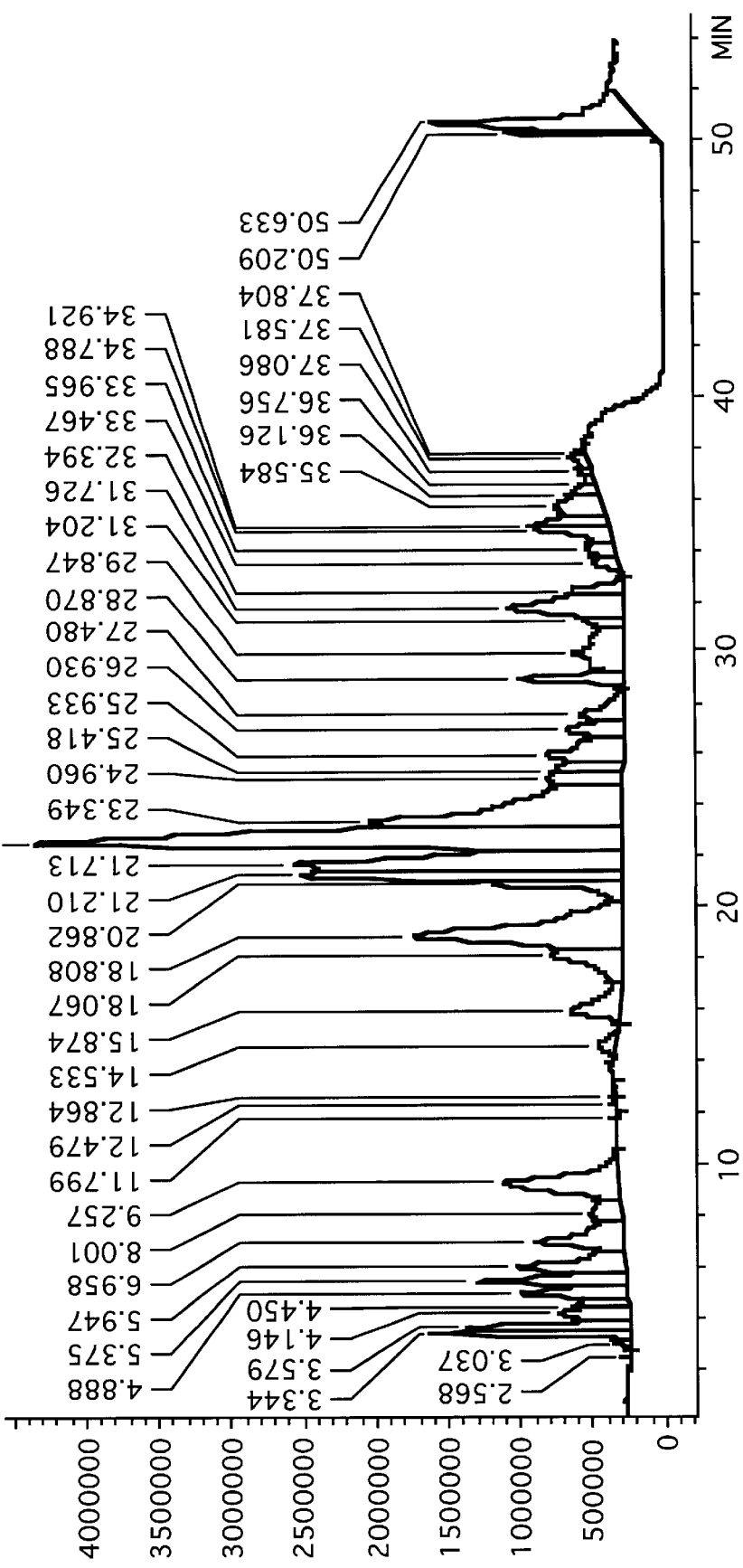
FIG. 5 is an LC-MS chromatograph showing the analysis of a 625 compound library.

By using a large number of carboxylic acids, the range of this system was tested. Twenty-five carboxylic acids were used to generate a 625 compound library, ignoring stereoisomers. An LC/MS trace of the organic solution showed a large number of mass ions corresponding to expected library constituents (FIG. 5). Although no attempt was made to exhaustively verify the presence of all 625 compounds, it is reasonable to assume that this system adequately generates a diverse library of compounds.

Example 3
Examination of the Reversibility of Palladium-Catalyzed Reaction

The reactivity of the identified palladium π-allyl system was tested to see what conditions would afford the best chance for success, as measured by extensive reaction lifetime, substitution with a large number of components, and additional palladium complexation of the esterified products.

A number of catalysts and solvents were evaluated, and the best results were derived from palladium tetrakistriphenylphosphine as the palladium source, triethylphosphite (P(OEt)$_3$) as a supporting ligand, and freshly distilled methylene chloride as the organic solvent. Triethylphosphite, which is already oxidized and diminishes the amount of phosphone present in the analysis, has a less intense ionization relative to triphenylphosphine, which facilitated analysis by increasing the visibility of the other absorbances.

In trying to examine the reactivity of the palladium reaction, a time-dependent NMR spectrum of the starting cyclopentene diacetate and 4-methoxyphenyl acetic acid (Scheme 3 below) was taken over fifty-six hours, under a nitrogen atmosphere, eliminating the problems associated with dissolved oxygen in the solvent (FIG. 4). Two singlets at 3.8 and 3.6 ppm, corresponding to the methoxy protons and the benzylic methylene protons, are present at t=0. After 12 hours, new peaks appear at 3.54 and 3.56 ppm. These likely correspond to the benzylic methylene peaks of homo- and hetero-substituted esters incorporating the 4-methoxy phenyl acetic acid. Over time, the proportion of the ester peaks relative to starting material increased, indicating reaction progress.

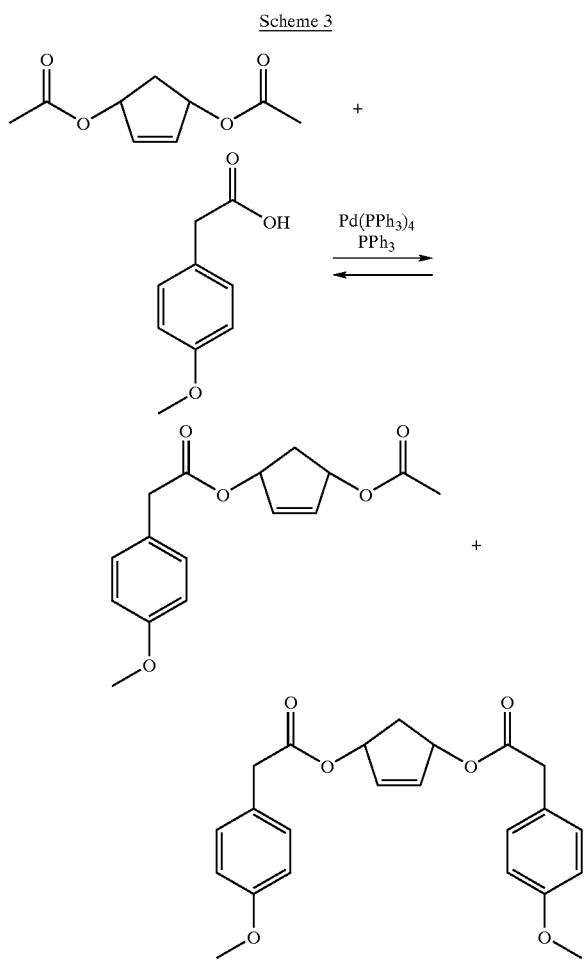

In attempting to demonstrate reversibility, the reaction was monitored by fluorescence (Scheme 4 below). Commercially available Wang resin was derivatized by reaction with 1,4-dibromocyclopent-2-ene in chloroform and acetylating with potassium acetate under phase transfer conditions. Resin bound 1-acetoxycyclopent-2-ene was then subjected to standard palladium π-allyl conditions in the presence of a fluorescent carboxylic acid (1-pyrene butyric acid). Upon examining the beads after twenty-four hours with a fluorescence microscope, fluorescence was observed (FIGS. 5A–B). A control experiment, where 1-pyrene butyric acid was added to un-derivatized Wang resin, was performed to test whether the beads were fluorescent due to covalent attachment, or some non-covalent interaction that caused the 1-pyrene butyric acid to adhere to the bead. Fluorescence was not observed in this case, demonstrating that pyrene was reacting in the manner expected for a palladium π-allyl system. Furthermore, when the fluorescent beads were exposed to a large excess of acetic acid under catalytic conditions, the fluorescence stopped, indicating a reversible reaction, or hydrolysis off the bead.

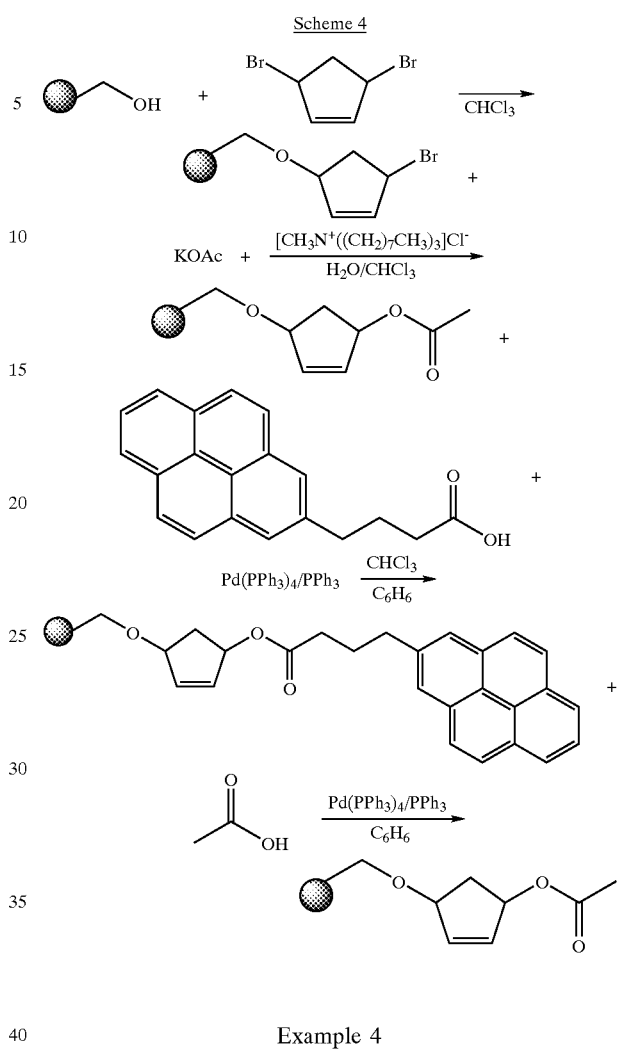

Example 4
Quantitative Analysis of Pd (0) Equilibrium & Lifetime

To investigate the equilibrium of the system in a more quantitative fashion, a model system of 1,4-diacetoxycyclopent-2-ene, methoxyphenyl acetic acid, the $Pd(PPh_3)/P(OEt)_3$ catalyst system, and distilled methylene chloride as the solvent were used. The methoxyphenyl acetic acid contains a chromophore, which enables analysis by ultraviolet spectroscopy. Aliquots were taken every eighty minutes for seven hours, anticipating that the mildly nucleophilic carboxylate would require a long reaction time, and injected on the HPLC-MS. The chromatogram at 274 nm, which corresponded to the methoxyphenyl acetic chromophore, was recorded for the reaction at five hours and forty minutes, because the reaction appeared to be complete well within that time frame. There were several interesting and unexpected results from this study as shown in Table 1 below.

TABLE 1

Peak Integration Data for Palladium Catalyzed Reactions

| Time (min) | Acid | Monosub. | Disub. | Monosub. | Total Product |
|---|---|---|---|---|---|
| 0 | 205 | 228 | 1022 | 162 | 1412 |
| 80 | 670 | 239 | 493 | 118 | 850 |
| 160 | 303 | 215 | 456 | 114 | 786 |

TABLE 1-continued

Peak Integration Data for Palladium Catalyzed Reactions

| Time (min) | Acid | Monosub. | Disub. | Monosub. | Total Product |
|---|---|---|---|---|---|
| 240 | 524 | 214 | 451 | 119 | 784 |
| 340 | 181 | 198 | 404 | 110 | 713 |
| 460 | 435 | 235 | 486 | 133 | 855 |

As indicated by the integral report, there is a relatively high total amount of product at the zero point, which was approximately fifteen minutes real time. It was expected that the 15 min lag time would be negligible for this reaction. However, because the highest total amount of product appears at the first time point, it was a significant amount of time. It also appears that equilibrium is reached quickly. Very small changes are observed, relative to the initial time points, for the remaining injections, meaning that a much shorter time scale needs to be utilized.

Despite its limitations, electrospray HPLC-MS seemed to be the most effective library analysis method. However, the technique should be viewed as, at best, semi-quantitative. Other groups using mass spectrometry as a quantitative tool typically run standard solutions for each compound at many concentrations ((Bi et al., "Mixed-Mechanism Ionization to Enhance Sensitivity in Atmospheric Pressure Ionization LC/MS," *J. Pharm. Biomed. Anal.* 22:861–867 (2000); Tuthill et al., "Quantitative Analysis of Thymosin α1 in Human Serum by LC-MS/MS," *AAPS PharmSciTech* 1 (2000), which are hereby incorporated by reference in their entirety). Furthermore, contaminants in the solutions, e.g., alkali metal ions present in commercial protein preparations, can significantly alter analyte ionizability. In the long run, LC-NMR may represent a more useful and quantitative tool for poorly ionizable libraries (Albert, "Liquid Chromatography-Nuclear Magnetic Resonance Spectroscopy," *J. Chromatogr. A.* 856:199–211 (1999); Wolfender et al., "LC/NMR in Natural Products Chemistry," *Curr. Org. Chem.* 2:575–596 (1998), which are hereby incorporated by reference in their entirety).

Figure 6:
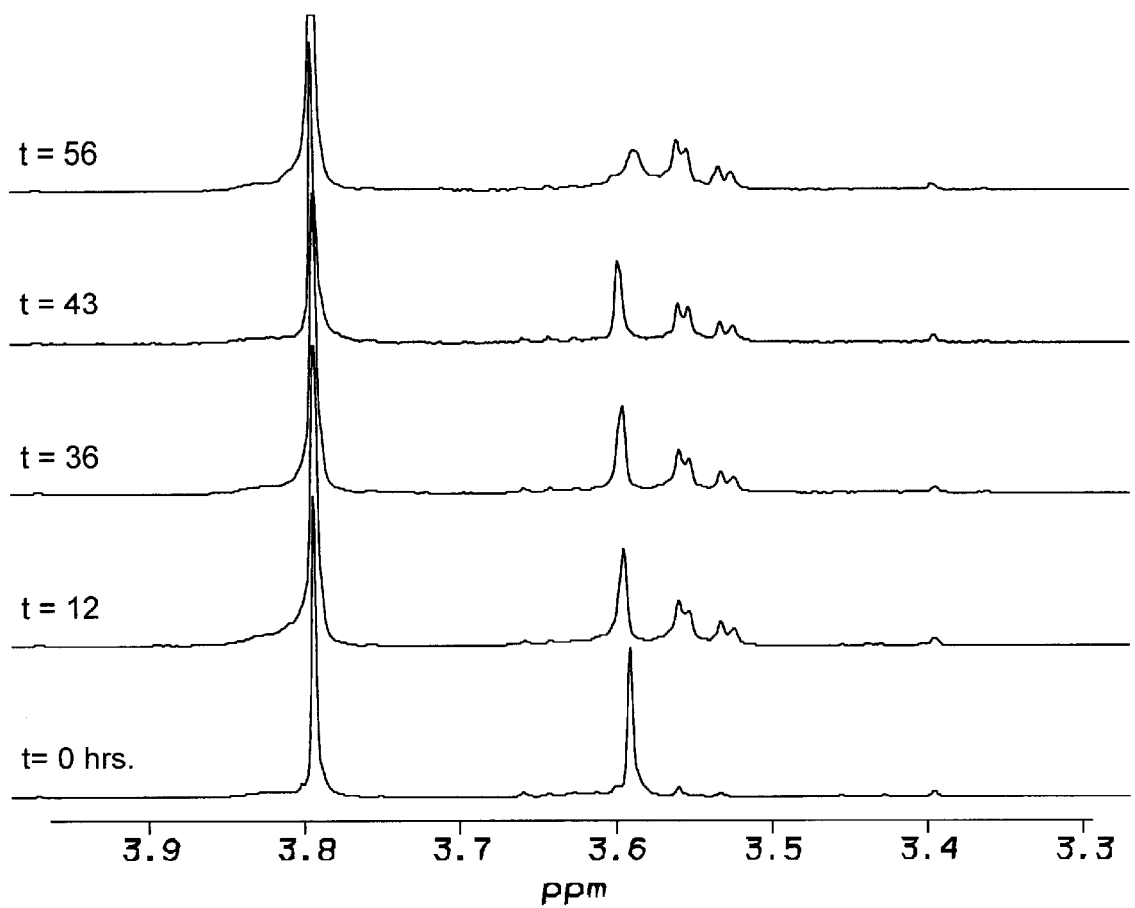
FIG. 6 is a time dependent $^1$H NMR of the reaction of 1,4-diacetoxycyclopent-2-ene and methoxyphenylacetic acid using a Pd (0) catalyst.

While trying to examine this particular system in more detail, it was found highly beneficial to use carboxylic acids that contain a chromophore that can be simultaneously analyzed by LC/MS and UV spectroscopy. The techniques complement each other nicely, and the UV is typically cleaner than the MS trace (FIGS. 6A–B). Using 1,4-diacetoxycyclopent-2-ene and p-methoxyphenyl acetic acid as a model system, it was possible to see peaks for the sodium adducts of the monosubstituted ester at thirteen and seventeen minutes, and the di-substituted ester at fifteen minutes. The masses were validated by correspondence with the chromatogram. Therefore, this system was used to optimize reaction conditions.

Perhaps more important than the extent of conversion for this reaction is the time period during which reaction can occur. If some substitution occurs, receptor binding can enrich a particular component as long as the catalyst remains active. One method for determining catalyst lifetime has been to add an additional component after a certain time period to see if additional reaction occurs (FIG. 7). A series of experiments where one equivalent of hydrocinnamic acid was added to the model reaction scheme at 1.5, 4, and 5.5 hours were performed. 5 μL aliquots were removed, filtered through chelex, and analyzed by HPLC-MS. The trace indicates catalyst is still active after 5.5 hours, by the appearance of peaks corresponding to 297 (14 min.) and 403 (17 min) in the chromatogram. These are sodium adducts of monosubstituted hydrocinnamic ester and the hetero-substituted bis ester, respectively, whose structures are illustrated in Scheme 5 below. However, it is possible that these peaks result from catalysis by acetate ion, formed in situ by palladium complexation.

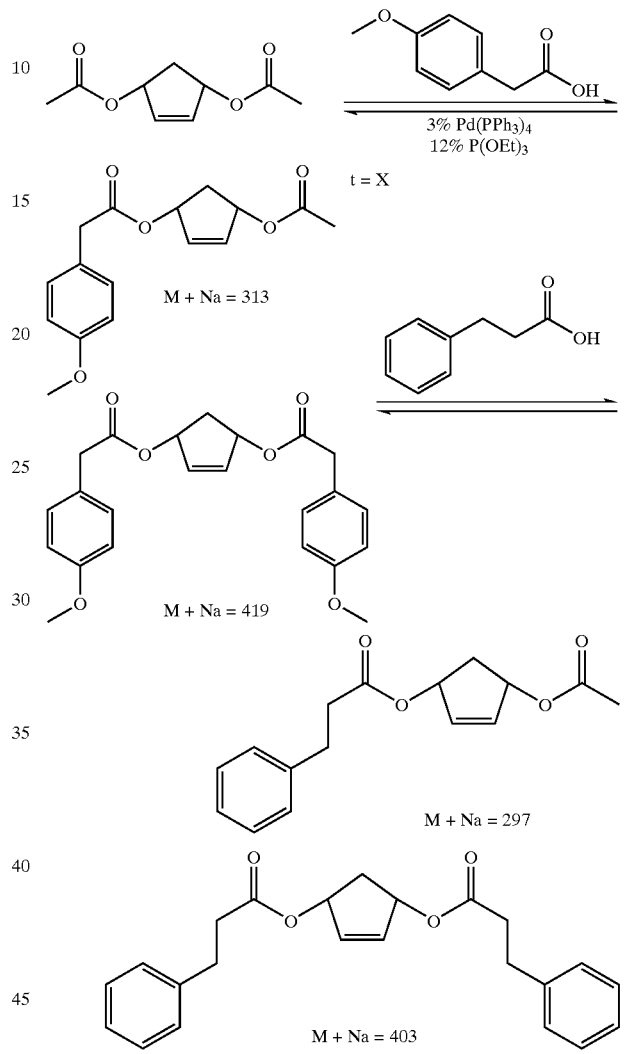

Scheme 5

A better way of determining catalyst lifetime under the reaction conditions is to allow the catalyst to stir by itself, so that the possibility of basic catalysis by acetate ion is eliminated. Tetrakis palladium triphenylphosphine and triethylphosphite was dissolved in methylene chloride to a concentration of 20 mM and allowed to stir at room temperature for eighteen hours under nitrogen atmosphere. At this point, 1,4-diaceteoxycyclopent-2-ene and methoxyphenyl acetic acid were added. As determined by LC/MS analysis, the presence of peaks at fourteen and seventeen minutes having ions (sodium adducts) of 313 (1-acetoxy-4-(methoxyphenylacetoxy)cyclopent-2-ene) and 419 (1,4-di-(methoxyphenylacetoxy)cyclopent-2-ene) indicated that the reaction was successful, demonstrating extended catalyst lifetime (FIG. 8A). In a control experiment using the same reagents without Pd catalyst, there are no peaks at fourteen and seventeen minutes, demonstrating the palladium dependence of the reaction (FIG. 8B).

Repeating the same experiment in the presence of water, using the LC-MS vial/centrifuge tube apparatus of FIG. 3A), peaks corresponding to the sodium adducts of 1-acetoxy-4-(methoxyphenylacetoxy)cyclopent-2-ene and 1,4-di(methoxyphenylacetoxy)cyclopent-2-ene are evident at fourteen and seventeen minutes (FIG. 9). Seeing active catalyst after eighteen hours in contact with water provided strong evidence that the system is robust enough for application to dynamic diversity.

Example 5

Cellulose Membrane Permeability to Reaction Products

One of the key components to this system is the physical separation between the organic chemistry and the biomolecular receptor. As a simple test, starting material was dissolved in methylene chloride at reaction concentration in an LC/MS vial, the vial covered with a cellulose membrane and immersed in glass-distilled, deionized water for twenty-four hours (FIGS. 10A–B). The experiment was analyzed by LC/MS. The 1,4-diacetoxy cyclopent-2-ene (3.5 minutes) and methoxyphenylacetic acid (2.8 minutes) partition themselves between the aqueous and organic layers, indicating sufficient ability to undergo membrane transport. Relative intensities from the two layers indicate an aqueous preference for the carboxylic acid (FIG. 10B), and an organic preference for the diacetate (FIG. 10A).

Figure 11:
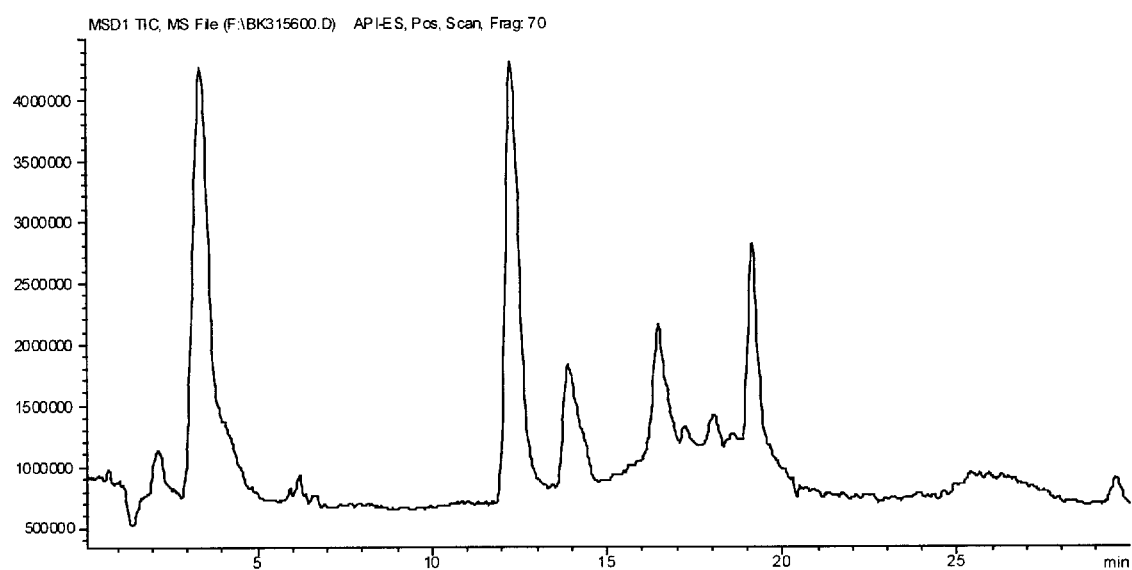
FIG. 11 illustrates palladium catalyst activity in the presence of water.
Figure 14:
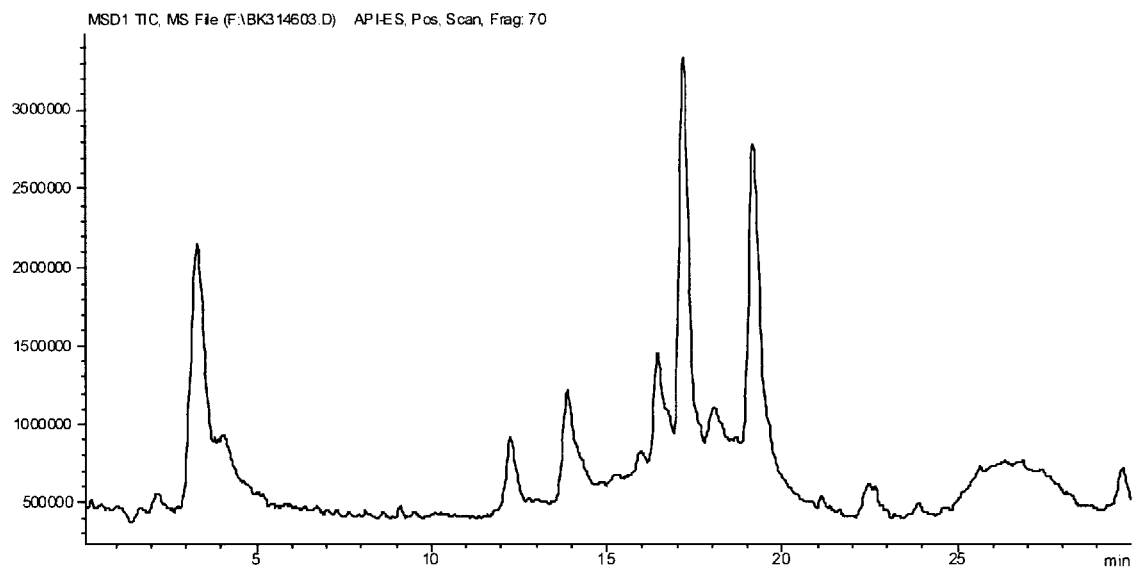
FIG. 14 is an LC-MS chromatograph which illustrates the stability of the palladium catalyst against π-allyl complex decomposition.
Figure 15:
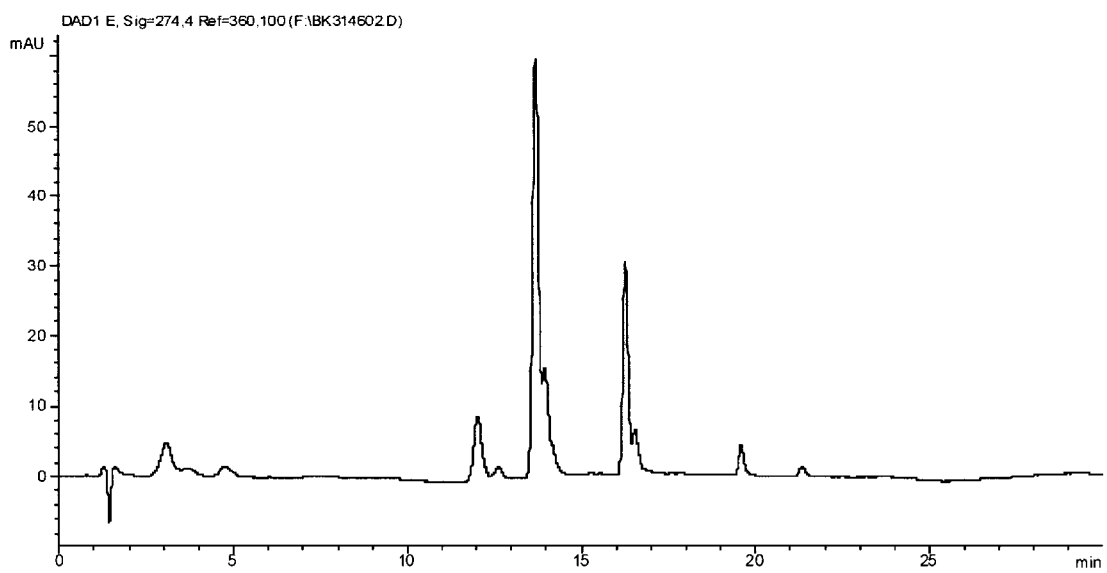
FIG. 15 is a chromatograph illustrating a base assisted palladium reaction.

Again using the model Pd-reaction, successful reaction with hydrocinnamic acid was demonstrated using the LC/MS vial reactor (FIG. 3A) immersed in water for forty-five minutes (FIGS. 11A–B). From this same experiment, it was demonstrated that products formed in the library will be able to cross the membrane and contact the receptor. The monosubstituted 1-acetoxy-4 -(methoxyphenylacetoxy) cyclopent-2-ene sodium adduct is present at thirteen minutes in the aqueous layer (FIG. 11B). Furthermore, enough of the compound is present to detect by LC/MS without having to concentrate the sample. This suggests that even ligands with strong preference for organic solvent will still partition themselves, and be detectable by this analysis method.

In the presence of deoxygenated water, the catalyst remains active for at least eighteen hours. Potentially, it will remain active as long as oxygen is excluded. Although rigorous calculation was not possible, eighteen hours was considered sufficient for multiple cycles of diffusion, passive transport, and affinity driven selection to alter equilibrium. Successfully demonstrating this mandates a reversible scrambling mechanism. Although not quantitatively proven, additional substitution of a pre-equilibrating system did occur. Seeing esterified products react within the context of pre-reacted system indicates that mixtures of esters will react with each other, generating diversity. Evidence of thermodynamic control was provided by a series of reactions involving 1,4-diacetoxycyclopent-2-ene and additional equivalents of methoxyphenylacetic acid (Scheme 6 and Table 2 below).

Scheme 6

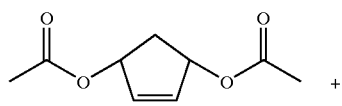

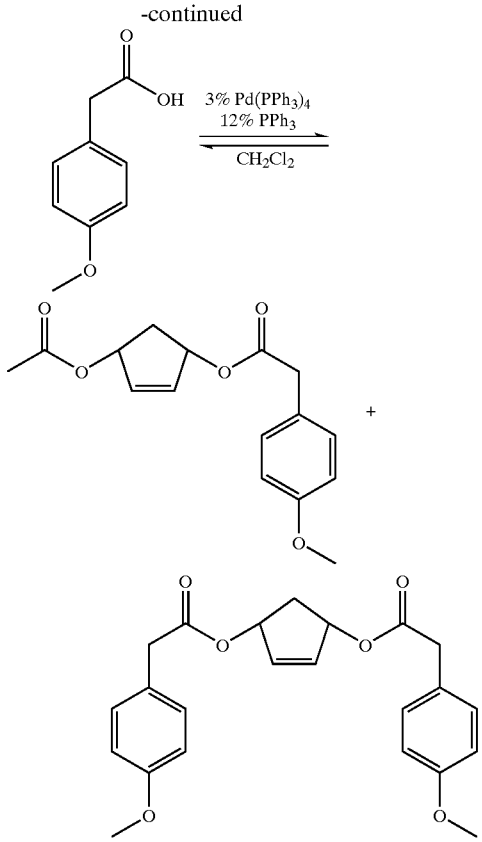

TABLE 2

Peak Integration Data Obtained When Using Excess Acid

| | Peak Integration Area (274 nm) | | |
|---|---|---|---|
| Equivalents of Acid | Free Acid | Mono-ester | Di-ester |
| 1 | 101 | 503 | 276 |
| 3 | 202 | 425 | 509 |
| 6 | 1382 | 287 | 831 |

As the equivalents of methoxyphenylacetic acid are increased, the amount of di-ester increased, as indicated by the integration area at 274 nm. A likely reason for this occurrence would be LeChatlier's principle; a shifting of the equilibrium in response to some perturbation.

Example 6

Palladium Catalyst Stability

Reaction yields were demonstrated to be low through previous NMR experiments. Although not completely prohibitive, low reaction yields complicate analysis by inhibiting detection. Furthermore, it becomes difficult to gauge how much receptor is required to enable selection. One potential danger resulting from poor conversion is the potential for π-allyl complex decomposition. Without the presence of adequate nucleophiles in solution to enact trapping, which a pool of carboxylate leaving groups may not be, π-allyl complex decomposition becomes a definite possibility. To test this, 1,4-diacetoxycyclopent-2-ene, tetrakis palladium triphenylphosphine and triethyl phosphite were incubated in methylene chloride for eighteen hours. Methoxyphenylacetic acid was then added as a methylene chloride solution to the mixture and the reaction monitored by LC/MS (FIG. 12). As indicated by peaks in the total ion chromatogram at fourteen and seventeen minutes, esterification is possible and the complete decomposition of the π-allyl complex does not occur.

Example 7
Increasing Conversion Rates

Efforts to increase the percent conversion were taken. Seeing evidence that the reaction could be driven toward product formation by adding additional equivalents of nucleophile, it was hypothesized that conversion was limited by the inherent nucleophilicity of the carboxylic acids. Tests to probe the effect of nucleophilic strength on the system were undertaken. Diazobicycloundecene (DBU), a base of sufficient strength to deprotonate carboxylic acids and activate them for nucleophilic attack, was incorporated into the model palladium system and reaction monitored by LC/MS (FIG. 13). The chromatogram monitored at 274 nm in the ultra-violet spectrometer, corresponding to the absorbance maximum of methoxyphenyl acetic acid, indicates significant excess of products (fourteen and seventeen minutes) relative to starting material. By comparison with the data for reaction with one equivalent of methoxyphenylacetic acid (Table 2 above), an increase in conversion is obtained by adding an equivalent of base, although quantitation with this system is unreliable. It appears that this system would be limited by the poor nucleophilicity of protonated carboxylic acid reagents.

Example 8
Construction of Tailored Libraries

Using the knowledge gained through studying the various components of this system, improved selection experiments were designed. Because of the detailed analysis of systems using only methoxyphenylacetic acid and hydrocinnamic acid, they were utilized in a nine compound reference library (Table 3 below).

TABLE 3

Expected Mass of Sodium Adducts for Nine-Compound Reference Library

| M + 23 | | acetic acid | methoxyphenyl acetic acid | hydro-cinnamic acid |
| --- | --- | --- | --- | --- |
|  |  | 59 | 165 | 149 |
| acetic acid | 59 | 207 | 313 | 297 |
| methoxyphenyl acetic acid | 165 | 313 | 419 | 403 |
| hydrocinnamic acid | 149 | 297 | 403 | 387 |

A second library consisting of ten carboxylic acids was also synthesized, providing one hundred twenty-one compounds, ignoring stereoisomers. A library of this size was expected to be manageable experimentally, yet large enough to create an array of structures.

Catalyst stability was studied extensively in control studies (see Example 6). From those studies, the catalyst could be expected to remain active for eighteen hours, as long as the reaction remained relatively oxygen free. Furthermore, continued reaction upon addition of a second reagent was observed, demonstrating the ability to generate a mixture. Dynamic diversity experiments would run for eighteen hours. This ensures that equilibration can occur throughout the experiment, and that selection is not governed by kinetic parameters.

Various factors contributed to the choice of concentrations for these experiments. Initially, reagent concentration was chosen based on typical organic reactions and data were analyzed after the experiment was completed. In these experiments there are many factors to be considered. Esters formed in this dynamic library are going to have an inherent preference for organic solvent. Although not directly relevant to methylene chloride, the calculated octanol/water partition value, logP, was used as a rough guide in determining concentrations to be used in this experiment. Values for 1,4-diacetoxycyclopent-2-ene, methoxyphenylacetic acid, hydrocinnamic acid, methoxyacetic acid and a variety of esters incorporating those acids, were calculated using Pallas software (Pallas Version 2.1 StandBy Software, Inc., Burlingame, Calif.). Calculated values range from 0.36 for 1,4-diacetoxycyclopent-2-ene, the lightest bis ester in the library, to 7.29 for 1,4-dimethoxyacetoxycyclopent-2-ene, the heaviest compound in the library. Generally, carboxylic acids had lower logP values than monosubstituted cyclopentenes, which were lower than di-substituted cyclopentenes.

Data from previous experiments indicated that adding additional equivalents of carboxylic acid pushes the equilibrium toward diesters (Table 2). The necessity of maximizing the equivalents of carboxylic acid while still obtaining an appreciable amount of compounds to satisfy logP constraints dictates an approximate reaction concentration range. In earlier experiments, it was observed that total carboxylic acid concentrations in excess of 2 M were difficult to obtain. Therefore, a six-fold excess of carboxylic acid (1.8 M) relative to 1,4-diacetoxycyclopent-2-ene (0.3 M) was employed. Using a higher concentration of 1,4-diacetoxycyclopent-2-ene with six equivalents of acids would begin pushing the solubility limits of the system. Assuming six equivalents of carboxylic acid were enough to push all of the starting material to products, and the heats of formation for the individual compounds were equivalent, the concentration of any one compound in methylene chloride would be 2.5 mM. If this compound had a log P of 1, it would be present in aqueous solution at a concentration of 250 $\mu$M, for a log P of 2, 25 $\mu$M, and for a log P of 5, a compound would be present at a concentration of 25 nM. For selection of one of these compounds to occur, this would in turn require that the compound have a dissociation constant ($K_d$) of better than 250 $\mu$M, 25 $\mu$M, or 25 nM, respectively, since the semiquantitative nature of our analysis necessitated that a large change in the total amount of compound present in the aqueous compartment occur.

It is advantageous to use an excess of receptor to maximize the selection potential. Considering the vast range of possible ester concentrations, multiple experiments with varying protein concentrations seemed appropriate. Two experiments, one using a trypsin concentration of 43 $\mu$M and a second using a trypsin concentration of 257 $\mu$M, were performed in duplicate for the reference library and the one-hundred twenty-one compound library. Expecting the majority of the esters to have a log P of 2 or higher, 43 $\mu$M should be sufficient to interact with esters formed in the experiment. A concentration of 257 $\mu$M would be appropriate for dramatic enrichment of a single high affinity ligand. A trypsin free control experiment was used as the zero point.

Figure 16:
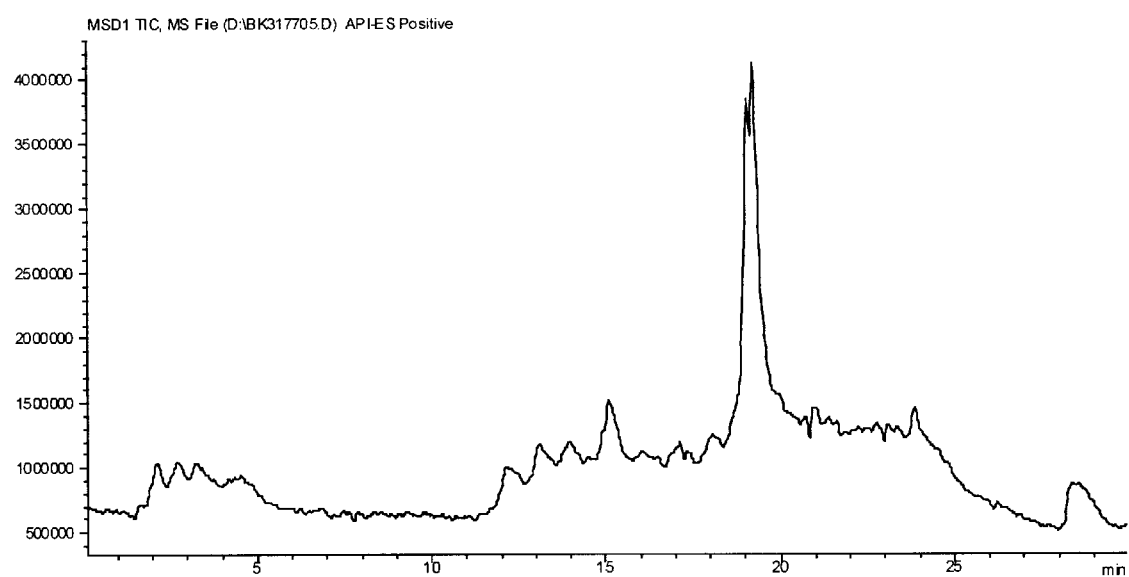
FIG. 16 is a chromatograph of the LC-MS analysis of the organic solution for a 121 compound library.

With the aforementioned criterion in mind, selection experiments were performed. The nine compound reference library and the one-hundred compound library were prepared under nitrogen (in the glove box) and allowed to equilibrate for one hour. They were then immersed in an LC-MS vial containing buffered aqueous solution (FIG. 3A). To maximize the amount of material available for analysis from the aqueous layer, a 10:1 ratio of water to methylene chloride was used. After 18 hours of incubation, an aliquot was removed from the organic layer and the aqueous samples concentrated for analysis. LC-MS analysis of the organic layer indicated product formation (FIG. 16).

Using the ability of the HPLC-mass spectrometer to extract individual ions from the total ion chromatogram, a number of ions were observed corresponding to expected library products. Importantly, several of the ions were found to vary in intensity in conjunction with changing protein concentrations. In particular, a strong correlation was observed between the amount of 1-acetoxy-4-(2-cyclopentene-1-acetoxy)cyclopent-2-ene and the presence of trypsin. While this observation has yet to be independently verified through the measurement of a binding or inhibition constant to trypsin, the results strongly support the suitability of reversible palladium π-allyl chemistry as a means of reversibly generating libraries of compounds under biphasic conditions, and of using such a system to amplify compounds via binding to a protein or enzyme.

Example 9
Generation of Dynamic Libraries of Homoallylamides by Olefin Metathesis A series of allyl- and homoallylamide derivatives of Boc-protected amino acids were prepared using standard coupling conditions (Scheme 7 and Table 4 below). Products were obtained in moderate to good yield; however, it should be noted that these procedures were unoptimized.

Scheme 7

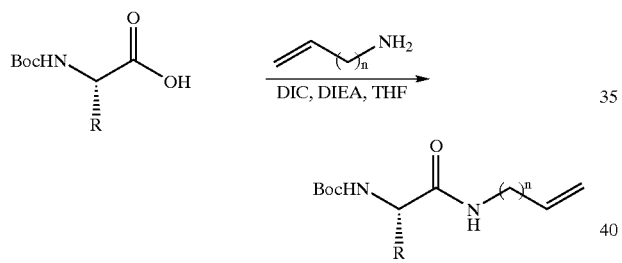

TABLE 4

Reaction Products and Yield for Products of Scheme 7

| Entry | R | n | Yield (%) |
|---|---|---|---|
| 1 | H | 2 | 83 |
| 2 | CH$_2$Ph (Phe) | 2 | 60 |
| 3 | CH$_2$Ind (Trp) | 2 | 67 |
| 4 | CH$_2$(NimTs)Im (His) | 2 | 55 |

These four homoallylamides were then dissolved to a total concentration of 500 mM in 400 microliters of methylene chloride, in a glass vial. To this was added 10 molar % of bis(tricyclohexylphosphine)benzylidine ruthenium (IV) dichloride. The vial was covered with a cellulose dialysis membrane (MWCO=1000 g/mol), and with a crimper cap. The vial was then added to a centrifuge tube containing 2 ml of a 1 millimolar solution of HIV protease in phosphate buffered saline solution, pH 7.4. This combined apparatus was shaken on a rotary platform for 24 temperature. The aqueous solution was then removed and guanidinium hydrochloride was added to a total concentration of 8 molar in order to denature the protease. This aqueous solution was then analyzed by HPLC-mass spectrometry.

Example 10
Generation of Dynamic Libraries of Acetals by a Resin-Immobilized Catalyst Ten alcohols and ten aldehydes are dissolved to a total concentration of 0.5 molar in 400 microliters of dichloromethane. This solution can be added to a vial containing 20 mg of Amberlite IRP-69 ion-exchange resin (Aldrich Chemical Co., cat. No. 27,427-5). The vial is then covered with dialysis membrane (MWCO=1,000 dalton) and capped with a crimper cap as described previously. The vial is subsequently immersed in a centrifuge tube containing 1.0 ml of protein kinase C and phosphatidylserine at a concentration of 0.1 molar in phosphate-buffered saline, pH 7.4. The solution is shaken on a rotary platform for 24 hours at room temperature, as described in Example 9 above.

Acetals, if any, having an affinity for the target molecule can be isolated from the aqueous solution in the centrifuge tube.

Example 11
Preparation of a Library of RNA-Binding Compounds Under Reversible Conditions Using a Nonspecific Lipase Ten amino alcohols (11.1–11.10) and four dicarboxylic acids (11.11–11.14) can be dissolved in 400 microliters of phosphate buffered saline, pH 7.4, and 100 mM potassium chloride, to a total concentration of 0.5 molar. To this is added 20 units of pig liver esterase. This solution can be added to a vial, which is then covered with a cellulose-based dialysis membrane (MWCO=1,000 dalton) and capped with a crimper cap as described previously. The vial is then immersed in a centrifuge tube containing 400 microliters of a 100 micromolar solution of an RNA oligonucleotide with the sequence 5'-UGAGCCUGGGAGCUCU-3' (SEQ. ID. No. 1) in phosphate buffered saline, pH 7.4, and 100 mM potassium chloride.

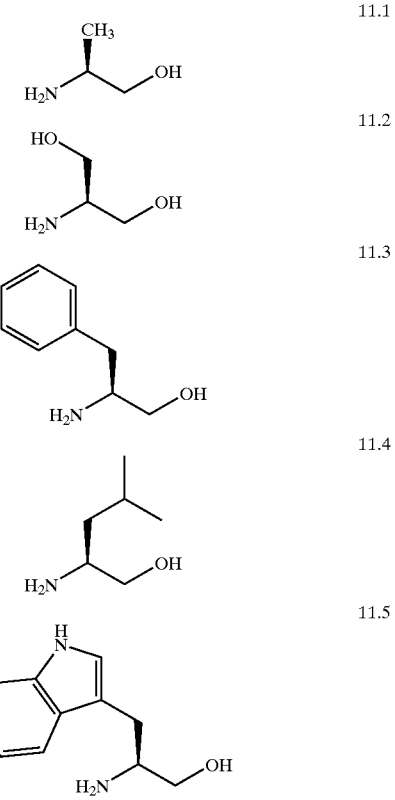

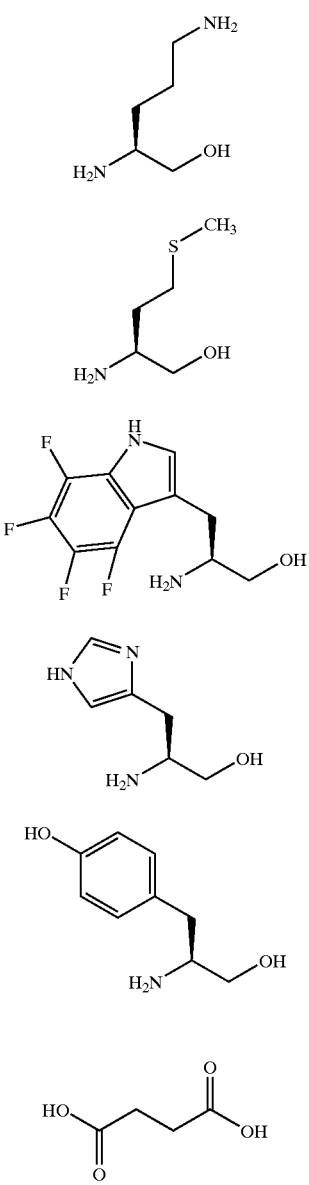

This solution is shaken on a rotary platform at room temperature for 12 hours. The vial containing the lipase solution is then removed, and the RNA-containing solution can be dialyzed against 10 ml buffer (PBS, pH 7.4, 100 mM KCl) for 12 hours. The dialysate should be retained, and the RNA-containing solution re-subjected to library selection (i.e., a fresh vial containing 11.6–11.14 and lipase in buffer is added to the RNA solution, and library selection allowed to proceed an additional 12 hours). After two more rounds of dialysis against buffer and subsequent library selection, the dialysates are combined, lyophilized, and analyzed by HPLC-mass spectrometry. In this manner, the total amount of highest-affinity compound is amplified through repeated rounds of dynamic selection.

Although the invention has been described in detail for purposes of illustration, it is to be understood that such detail is solely for that purpose, and variations can be made therein by those skilled in the art without departing from the spirit and scope of the invention which is defined by the following claims.

What is claimed:

1. A method of identifying a ligand having affinity for a target molecule comprising:

providing in first and second trials a dual-chambered reaction vessel comprising first and second containers defining first and second chambers, respectively, which are separated by a semipermeable membrane, with the first chamber comprising an organic solvent and a plurality of reactants which form a combinatorial library of products, the second chamber comprising an aqueous solvent immiscible in the organic solvent and, during the first trial but not the second trial, a target molecule, and the semipermeable membrane being permeable to one or more products of the combinatorial library of products;

identifying any products present in the second chamber at higher concentration during the first trial as compared to the second trial.

2. The method according to claim 1, wherein said identifying comprises:

performing liquid chromatography-mass spectroscopy on the contents removed from the second chamber for the first and second trials and determining whether the spectroscopy results differ for the first and second trials by defining differential peaks.

3. The method according to claim 2, wherein the determining comprises:

assigning mass spectroscopy peaks to predicted combinatorial library products and matching assigned mass spectroscopy peaks to the differential peaks.

4. The method according to claim 3, wherein the removing is carried out between about 20 minutes and about 24 hours following the providing.

5. The method according to claim 1 further comprising:

removing the contents of the second chamber prior to the identifying.

* * * * *

SEQUENCE LISTING

<160> NUMBER OF SEQ ID NOS: 1

<210> SEQ ID NO 1
<211> LENGTH: 16
<212> TYPE: RNA
<213> ORGANISM: Artificial Sequence
<220> FEATURE:
<223> OTHER INFORMATION: Description of Artificial Sequence:  artificial target molecule

<400> SEQUENCE: 1
ugagccuggg agcucu                                                         16